US007531505B2

(12) United States Patent
Hamilton et al.

(10) Patent No.: US 7,531,505 B2
(45) Date of Patent: May 12, 2009

(54) COMPOSITIONS AND METHODS FOR PROMOTING ATTACHMENT OF CELLS OF ENDOTHELIAL CELL LINEAGE TO MEDICAL DEVICES

(75) Inventors: Paul Theodore Hamilton, Cary, NC (US); Daniel James Kenan, Chapel Hill, NC (US); Amy Katherine Solan, Durham, NC (US)

(73) Assignee: Affinergy, Inc., Durham, NC (US)

( * ) Notice: Subject to any disclaimer, the term of this patent is extended or adjusted under 35 U.S.C. 154(b) by 0 days.

(21) Appl. No.: 11/649,935

(22) Filed: Jan. 5, 2007

(65) Prior Publication Data

US 2007/0166350 A1 Jul. 19, 2007

Related U.S. Application Data

(60) Provisional application No. 60/758,029, filed on Jan. 11, 2006.

(51) Int. Cl.
*A61K 38/00* (2006.01)
*A61F 2/04* (2006.01)

(52) U.S. Cl. .......................... 514/2; 623/1.15; 424/423

(58) Field of Classification Search ...................... None
See application file for complete search history.

(56) References Cited

U.S. PATENT DOCUMENTS

| 5,498,538 | A | 3/1996 | Kay et al. |
| 5,635,482 | A | 6/1997 | Bhatnagar |
| 5,643,712 | A | 7/1997 | Brasile |
| 5,744,515 | A | 4/1998 | Clapper |
| 5,866,363 | A | 2/1999 | Pieczenik |
| 5,929,060 | A | 7/1999 | Araneo |
| 6,140,127 | A | 10/2000 | Sprague |
| 6,180,084 | B1 | 1/2001 | Ruoslahti et al. |
| 6,280,760 | B1 | 8/2001 | Meyer et al. |
| 6,436,132 | B1 | 8/2002 | Patel et al. |
| 6,559,126 | B2 | 5/2003 | Tournaire et al. |
| 6,733,755 | B2 | 5/2004 | Tchistiakova et al. |
| 6,897,218 | B2 | 5/2005 | Casella et al. |
| 6,974,791 | B2 | 12/2005 | Wong et al. |
| 7,037,332 | B2 | 5/2006 | Kutryk et al. |
| 2002/0049495 | A1 | 4/2002 | Kutryk et al. |
| 2003/0166004 | A1 | 9/2003 | Gyuris et al. |
| 2003/0185870 | A1 | 10/2003 | Grinstaff et al. |
| 2003/0203038 | A1 | 10/2003 | Vail |
| 2003/0229393 | A1 | 12/2003 | Kutryk et al. |
| 2004/0127640 | A1 | 7/2004 | Belcher et al. |
| 2004/0258726 | A1 | 12/2004 | Stupp et al. |
| 2005/0043787 | A1 | 2/2005 | Kutryk et al. |
| 2005/0085623 | A1 | 4/2005 | Balian |
| 2005/0187162 | A1 | 8/2005 | Dhanaraj |
| 2006/0153775 | A1 | 7/2006 | Von Wronski et al. |
| 2006/0223756 | A1 | 10/2006 | Liau et al. |

FOREIGN PATENT DOCUMENTS

WO  WO/03/014145  2/2003

OTHER PUBLICATIONS

Binetruy-Tournaire et al., "Identification of a peptide blocking VEGF-meidated angiogenesis"; EMBO Journal, vol. 19, No. 7, pp. 1525-1533, 2000.
Giordano et al., "Biopanning and rapid analysis of selective interactive ligands"; Nature Medicine, vol. 7, No. 11, pp. 12491253, 2001.
Hetian et al., "A novel peptide isolated from a phage display library inhibits tumor growth and metastasis by blocking the binding of VEGF to its kinase domain receptor"; Journal of Biological Chemistry, vol. 277, No. 45, pp. 43137-43142, 2002.
El-Mousawi et al., "A VEGF high affinity receptor 1-specific peptide with antiangiogenic activity identified using a phage display library"; Journal of Biological Chemistry, vol. 278, No. 21, pp. 46681-46691, 2003.
Zhi et al., "Characterization of a specific phage-displayed peptide binding to vasculature of human gastric cancer"; Cancer Biology & Therapy, vol. 3, No. 12, pp. 1232-1235, 2004.
D'Andrea et al., "Targeting angiogenesis: structural characterization and biological properties of a de novo engineered VEGF mimicking peptide"; PNAS, vol. 102, No. 40, pp. 14215-14220, 2005.
Guo et al., "Identification of peptides inhibiting adhesion of monocytes to the injured vascular endothelial cells through phage-displaying screening"; Acta Biochim Biophys Sina (Shanghai), vol. 37, No. 4, pp. 227-233, 2005, Note: only Abstract was available.
Whaley et al., "Selection of peptides with semiconductor binding specificity for directed nanocrystal assembly"; Nature, 405: 665-668, 2000.
Gilbert et al., "Chimeric peptides of statherin and osteopontin that bind hydroxyapatite and mediate cell adhesion"; The Journal of Biological Chemistry, 275(21): 16213-16218, 2000.
Kenausis et al., J. Phys. Chem B., Mar. 2000, 104 (14):3298-309. Poly(Lys)-PEG Layers on Metal Oxide Surfaces: Attachment Mechanism and Effects of Polymer Architecture . . . .
International Preliminary Report on Patentability for PCT/US2007/000517, Jul. 24, 2008.
International Preliminary Report on Patentability for PCT/US2007/000518, Jul. 24, 2008.
Written Opinion of the International Searching Authority for PCT/US08/61200, Sep. 29, 2008.

*Primary Examiner*—Anand U Desai
(74) *Attorney, Agent, or Firm*—Laura L. Kiefer

(57) ABSTRACT

The present invention provides compositions and methods for an improved coating for medical devices. Provided is a biofunctional coating composition comprising at least one binding domain that has binding specificity for a metallic surface material of a medical device, and at least one binding domain that has binding specificity for cells of endothelial cell lineage. Methods for coating a metallic surface of a medical device, and for manufacturing of a medical device, comprise contacting the metallic surface to be coated with the biofunctional coating material in an amount effective to form a coating, and may further comprise contacting the coated surface with cells of endothelial cell lineage to bind the cells of endothelial cell lineage to the coated surface.

22 Claims, No Drawings

SEQUENCE LISTING

```
<160> NUMBER OF SEQ ID NOS: 50

<210> SEQ ID NO 1
<211> LENGTH: 39
<212> TYPE: PRT
<213> ORGANISM: Artificial
<220> FEATURE:
<223> OTHER INFORMATION: synthesized

<400> SEQUENCE: 1

Ser Gly Val Val Asp Ala Gly Val Val Ala Glu Asp Gly Val Ser Gly
1               5                   10                  15

Glu Ala Ser Arg Ser Ser His Arg Thr Asn His Lys Lys Asn Asn Pro
            20                  25                  30

Lys Lys Lys Asn Lys Thr Arg
        35

<210> SEQ ID NO 2
<211> LENGTH: 39
<212> TYPE: PRT
<213> ORGANISM: Artificial
<220> FEATURE:
<223> OTHER INFORMATION: synthesized

<400> SEQUENCE: 2

Ser Val Glu Val Ala Cys Val Ser Ala Gly Gly Gly Ser Ser Asp Val
1               5                   10                  15

Cys Ala Ser Arg Asn His Thr Ile Ser Lys Asn His Lys Lys Lys Asn
            20                  25                  30

Lys Asn Ser Asn Lys Thr Arg
        35

<210> SEQ ID NO 3
<211> LENGTH: 19
<212> TYPE: PRT
<213> ORGANISM: Artificial
<220> FEATURE:
<223> OTHER INFORMATION: synthesized

<400> SEQUENCE: 3

Ser Ser His Arg Thr Asn His Lys Lys Asn Asn Pro Lys Lys Lys Asn
1               5                   10                  15

Lys Thr Arg
```

```
<210> SEQ ID NO 4
<211> LENGTH: 19
<212> TYPE: PRT
<213> ORGANISM: Artificial
<220> FEATURE:
<223> OTHER INFORMATION: synthesized

<400> SEQUENCE: 4

Asn His Thr Ile Ser Lys Asn His Lys Lys Asn Lys Asn Ser Asn
1               5                   10                  15

Lys Thr Arg

<210> SEQ ID NO 5
<211> LENGTH: 16
<212> TYPE: PRT
<213> ORGANISM: Artificial
<220> FEATURE:
<223> OTHER INFORMATION: synthesized
<220> FEATURE:
<221> NAME/KEY: MISC_FEATURE
<222> LOCATION: (1)..(1)
<223> OTHER INFORMATION: X is K, N, or S; preferably either K or N.
<220> FEATURE:
<221> NAME/KEY: MISC_FEATURE
<222> LOCATION: (3)..(4)
<223> OTHER INFORMATION: X = any amino acid
<220> FEATURE:
<221> NAME/KEY: MISC_FEATURE
<222> LOCATION: (5)..(7)
<223> OTHER INFORMATION: X is K, N, or H.
<220> FEATURE:
<221> NAME/KEY: MISC_FEATURE
<222> LOCATION: (9)..(10)
<223> OTHER INFORMATION: X is K, N, or S; preferably K or N.
<220> FEATURE:
<221> NAME/KEY: MISC_FEATURE
<222> LOCATION: (11)..(11)
<223> OTHER INFORMATION: X = any amino acid
<220> FEATURE:
<221> NAME/KEY: MISC_FEATURE
<222> LOCATION: (13)..(14)
<223> OTHER INFORMATION: X is K, N, or S; preferably K or N.

<400> SEQUENCE: 5

Xaa His Xaa Xaa Xaa Xaa Xaa Lys Xaa Xaa Xaa Lys Xaa Xaa Asn Lys
1               5                   10                  15

<210> SEQ ID NO 6
<211> LENGTH: 19
<212> TYPE: PRT
<213> ORGANISM: Artificial
<220> FEATURE:
<223> OTHER INFORMATION: synthesized
<220> FEATURE:
<221> NAME/KEY: MISC_FEATURE
<222> LOCATION: (1)..(19)
<223> OTHER INFORMATION: amino acids are D-amino acids

<400> SEQUENCE: 6

Ser Ser His Arg Thr Asn His Lys Lys Asn Asn Pro Lys Lys Lys Asn
1               5                   10                  15

Lys Thr Arg

<210> SEQ ID NO 7
<211> LENGTH: 40
<212> TYPE: PRT
<213> ORGANISM: Artificial
<220> FEATURE:
<223> OTHER INFORMATION: synthesized
```

```
<220> FEATURE:
<221> NAME/KEY: MISC_FEATURE
<222> LOCATION: (20)..(20)
<223> OTHER INFORMATION: linked to amino acid linker, KGGK
<220> FEATURE:
<221> NAME/KEY: MISC_FEATURE
<222> LOCATION: (21)..(21)
<223> OTHER INFORMATION: free amino terminus of second chain of
      divalent molecule
<220> FEATURE:
<221> NAME/KEY: MISC_FEATURE
<222> LOCATION: (40)..(40)
<223> OTHER INFORMATION: linked to same amino acid linker, KGGK, as
      amino acid residue 20

<400> SEQUENCE: 7

Ser Ser His Arg Thr Asn His Lys Lys Asn Asn Pro Lys Lys Lys Asn
1               5                   10                  15

Lys Thr Arg Gly Ser Ser His Arg Thr Asn His Lys Lys Asn Asn Pro
            20                  25                  30

Lys Lys Lys Asn Lys Thr Arg Gly
        35                  40

<210> SEQ ID NO 8
<211> LENGTH: 80
<212> TYPE: PRT
<213> ORGANISM: Artificial
<220> FEATURE:
<223> OTHER INFORMATION: synthesized
<220> FEATURE:
<221> NAME/KEY: MISC_FEATURE
<222> LOCATION: (20)..(20)
<223> OTHER INFORMATION: linked to amino acid linker, KKGGK, in
      forming first chain of tetravalent molecule
<220> FEATURE:
<221> NAME/KEY: MISC_FEATURE
<222> LOCATION: (21)..(21)
<223> OTHER INFORMATION: free N-terminal amino acid of second chain of
      tetravalent molecule
<220> FEATURE:
<221> NAME/KEY: MISC_FEATURE
<222> LOCATION: (40)..(40)
<223> OTHER INFORMATION: linked to amino acid linker, KKGGK, in forming
      second chain of tetravalent molecule
<220> FEATURE:
<221> NAME/KEY: MISC_FEATURE
<222> LOCATION: (41)..(41)
<223> OTHER INFORMATION: free N-terminal amino acid of third chain of
      tetravalent molecule
<220> FEATURE:
<221> NAME/KEY: MISC_FEATURE
<222> LOCATION: (60)..(60)
<223> OTHER INFORMATION: linked to amino acid linker, KKGGL, in forming
      third chain of tetravalent molecule
<220> FEATURE:
<221> NAME/KEY: MISC_FEATURE
<222> LOCATION: (61)..(61)
<223> OTHER INFORMATION: free N-terminal amino acid of fourth chain of
      tetravalent molecule
<220> FEATURE:
<221> NAME/KEY: MISC_FEATURE
<222> LOCATION: (80)..(80)
<223> OTHER INFORMATION: linked to amino acid linker, KKGGK, in forming
      fourth chain of tetravalent molecule

<400> SEQUENCE: 8

Ser Ser His Arg Thr Asn His Lys Lys Asn Asn Pro Lys Lys Lys Asn
1               5                   10                  15

Lys Thr Arg Gly Ser Ser His Arg Thr Asn His Lys Lys Asn Asn Pro
            20                  25                  30

Lys Lys Lys Asn Lys Thr Arg Gly Ser Ser His Arg Thr Asn His Lys
        35                  40                  45
```

-continued

```
Lys Asn Asn Pro Lys Lys Asn Lys Thr Arg Gly Ser Ser His Arg
    50              55                  60

Thr Asn His Lys Lys Asn Asn Pro Lys Lys Lys Asn Lys Thr Arg Gly
65                  70                  75                  80

<210> SEQ ID NO 9
<211> LENGTH: 17
<212> TYPE: PRT
<213> ORGANISM: Artificial
<220> FEATURE:
<223> OTHER INFORMATION: synthesized

<400> SEQUENCE: 9

Gly Val Asp Glu Trp Val Gly Ser Ser Cys Ala Gly Val Glu Glu Cys
1               5                   10                  15

Tyr

<210> SEQ ID NO 10
<211> LENGTH: 17
<212> TYPE: PRT
<213> ORGANISM: Artificial
<220> FEATURE:
<223> OTHER INFORMATION: synthesized

<400> SEQUENCE: 10

Leu Phe Ser Ser Ala Phe Val Phe Gly Ala Leu Ala Gly Ser Gly Ala
1               5                   10                  15

Gly

<210> SEQ ID NO 11
<211> LENGTH: 17
<212> TYPE: PRT
<213> ORGANISM: Artificial
<220> FEATURE:
<223> OTHER INFORMATION: synthesized

<400> SEQUENCE: 11

Phe Phe Gly Ala Asp Ser Tyr Leu Gly Gly Ser Phe Ala Ser Ala Phe
1               5                   10                  15

Asp

<210> SEQ ID NO 12
<211> LENGTH: 17
<212> TYPE: PRT
<213> ORGANISM: Artificial
<220> FEATURE:
<223> OTHER INFORMATION: synthesized

<400> SEQUENCE: 12

Gly Asp Val Ala Ala Ser Phe Phe Ala Ser Ala Ala Ser Ala Phe Ser
1               5                   10                  15

Val

<210> SEQ ID NO 13
<211> LENGTH: 17
<212> TYPE: PRT
<213> ORGANISM: Artificial
<220> FEATURE:
<223> OTHER INFORMATION: synthesized
```

-continued

```
<400> SEQUENCE: 13

Leu Ala Gly Ala Gly Trp Asp Ala Val Val Gly Gly Glu Gly Ala Val
1               5                   10                  15

Gly

<210> SEQ ID NO 14
<211> LENGTH: 17
<212> TYPE: PRT
<213> ORGANISM: Artificial
<220> FEATURE:
<223> OTHER INFORMATION: synthesized

<400> SEQUENCE: 14

Ala Gly Ser Ser Ser Ser Val Ser Phe Val Ala Ala Ala Gly Ser Ala
1               5                   10                  15

Val

<210> SEQ ID NO 15
<211> LENGTH: 17
<212> TYPE: PRT
<213> ORGANISM: Artificial
<220> FEATURE:
<223> OTHER INFORMATION: synthesized

<400> SEQUENCE: 15

Ala Val Phe Val Ala Asp Val Leu Gly Glu Glu Phe Val Gly Ala Val
1               5                   10                  15

Ala

<210> SEQ ID NO 16
<211> LENGTH: 17
<212> TYPE: PRT
<213> ORGANISM: Artificial
<220> FEATURE:
<223> OTHER INFORMATION: synthesized

<400> SEQUENCE: 16

Gly Val Gly Tyr Gly Trp Tyr Ser Val Ala Ala Ser Ser Val Val Ser
1               5                   10                  15

Ala

<210> SEQ ID NO 17
<211> LENGTH: 17
<212> TYPE: PRT
<213> ORGANISM: Artificial
<220> FEATURE:
<223> OTHER INFORMATION: synthesized

<400> SEQUENCE: 17

Pro Phe His Thr Gly Ala Phe Leu Trp Pro Glu Ser His Ser His Ser
1               5                   10                  15

His

<210> SEQ ID NO 18
<211> LENGTH: 14
<212> TYPE: PRT
<213> ORGANISM: Artificial
<220> FEATURE:
<223> OTHER INFORMATION: synthesized

<400> SEQUENCE: 18

Ser Glu Tyr Trp Ser Val Gly Ser Val Phe Ala Gly Ser Ser
1               5                   10
```

```
<210> SEQ ID NO 19
<211> LENGTH: 18
<212> TYPE: PRT
<213> ORGANISM: Artificial
<220> FEATURE:
<223> OTHER INFORMATION: synthesized

<400> SEQUENCE: 19

Phe Tyr Gly Glu Val Gly Tyr Val Gly Ala Ser Leu Tyr Ala Gly Gly
1               5                   10                  15

Ala Ser

<210> SEQ ID NO 20
<211> LENGTH: 17
<212> TYPE: PRT
<213> ORGANISM: Artificial
<220> FEATURE:
<223> OTHER INFORMATION: synthesized

<400> SEQUENCE: 20

Val Val Glu Ser Ser Ala Ala Tyr Ala Ser Ala Ser Ser Phe Ala Val
1               5                   10                  15

Val

<210> SEQ ID NO 21
<211> LENGTH: 17
<212> TYPE: PRT
<213> ORGANISM: Artificial
<220> FEATURE:
<223> OTHER INFORMATION: synthesized

<400> SEQUENCE: 21

Phe Glu Gly Ala Ser Val Ala Ser Leu Ala Phe Ala Gly Ser Val Ala
1               5                   10                  15

Gly

<210> SEQ ID NO 22
<211> LENGTH: 17
<212> TYPE: PRT
<213> ORGANISM: Artificial
<220> FEATURE:
<223> OTHER INFORMATION: synthesized

<400> SEQUENCE: 22

Val Gly Ala Val Ser Ser Ser Leu Ser Glu Glu Phe Leu Gly Ser
1               5                   10                  15

Leu

<210> SEQ ID NO 23
<211> LENGTH: 17
<212> TYPE: PRT
<213> ORGANISM: Artificial
<220> FEATURE:
<223> OTHER INFORMATION: synthesized

<400> SEQUENCE: 23

Tyr Val Gly Ser Ala Phe Ser Ala Ala Val Ala Ser Ser Val Ser Glu
1               5                   10                  15

Gly

<210> SEQ ID NO 24
<211> LENGTH: 17
<212> TYPE: PRT
<213> ORGANISM: Artificial
```

```
<220> FEATURE:
<223> OTHER INFORMATION: synthesized

<400> SEQUENCE: 24

Trp Ala Gly Ala Gly Ser Gly Gly Val Ala Trp Ser Ala Asp Phe Gly
1               5                   10                  15
Val

<210> SEQ ID NO 25
<211> LENGTH: 17
<212> TYPE: PRT
<213> ORGANISM: Artificial
<220> FEATURE:
<223> OTHER INFORMATION: synthesized

<400> SEQUENCE: 25

Ser Ala Asp Val Ser Ala Ala Leu Leu Val Leu Gly Ala Ser Glu Val
1               5                   10                  15
Leu

<210> SEQ ID NO 26
<211> LENGTH: 17
<212> TYPE: PRT
<213> ORGANISM: Artificial
<220> FEATURE:
<223> OTHER INFORMATION: synthesized

<400> SEQUENCE: 26

Phe Ala Val Tyr Cys Ala Ser Leu Ser Gly Val Cys Ser Ala Ser Phe
1               5                   10                  15
Glu

<210> SEQ ID NO 27
<211> LENGTH: 17
<212> TYPE: PRT
<213> ORGANISM: Artificial
<220> FEATURE:
<223> OTHER INFORMATION: synthesized

<400> SEQUENCE: 27

Ala Gly Ser Ser Ala Phe Ser Val Val Ala Ser Ser Val Ser Val Gly
1               5                   10                  15
Gly

<210> SEQ ID NO 28
<211> LENGTH: 13
<212> TYPE: PRT
<213> ORGANISM: Artificial
<220> FEATURE:
<223> OTHER INFORMATION: synthesized

<400> SEQUENCE: 28

Tyr Phe Arg Asp Ala Thr Pro Ala Val Phe Gly Tyr Trp
1               5                   10

<210> SEQ ID NO 29
<211> LENGTH: 17
<212> TYPE: PRT
<213> ORGANISM: Artificial
<220> FEATURE:
<223> OTHER INFORMATION: synthesized
```

```
<400> SEQUENCE: 29

Ala Tyr Glu Asp Gly Phe Tyr Ser Ser Gly Val Val Ser Ser Asp Trp
1               5                   10                  15

Val

<210> SEQ ID NO 30
<211> LENGTH: 16
<212> TYPE: PRT
<213> ORGANISM: Artificial
<220> FEATURE:
<223> OTHER INFORMATION: synthesized

<400> SEQUENCE: 30

Val Ser Gly Phe Gly Phe Ser Asp Ser Gly Ala Gly Glu Gly Val Phe
1               5                   10                  15

<210> SEQ ID NO 31
<211> LENGTH: 17
<212> TYPE: PRT
<213> ORGANISM: Artificial
<220> FEATURE:
<223> OTHER INFORMATION: synthesized

<400> SEQUENCE: 31

Gly Ala Trp Leu Val Ser Ala Leu Ile Glu Arg Gly Val Gly Ala Gln
1               5                   10                  15

Trp

<210> SEQ ID NO 32
<211> LENGTH: 17
<212> TYPE: PRT
<213> ORGANISM: Artificial
<220> FEATURE:
<223> OTHER INFORMATION: synthesized

<400> SEQUENCE: 32

Val Val Phe Ala Ala Ser Gly Val Ala Ala Asp Ala Gly Trp Ser Val
1               5                   10                  15

Ser

<210> SEQ ID NO 33
<211> LENGTH: 17
<212> TYPE: PRT
<213> ORGANISM: Artificial
<220> FEATURE:
<223> OTHER INFORMATION: synthesized

<400> SEQUENCE: 33

Gln Met Arg Glu Cys Asp Asp Cys Cys Cys Met Val Leu Pro Phe Thr
1               5                   10                  15

Ser

<210> SEQ ID NO 34
<211> LENGTH: 16
<212> TYPE: PRT
<213> ORGANISM: Artificial
<220> FEATURE:
<223> OTHER INFORMATION: synthesized

<400> SEQUENCE: 34

His Asn Ser Pro Phe Phe Leu Asp Cys Asn Phe Asp Ala Pro Cys Leu
1               5                   10                  15
```

```
<210> SEQ ID NO 35
<211> LENGTH: 17
<212> TYPE: PRT
<213> ORGANISM: Artificial
<220> FEATURE:
<223> OTHER INFORMATION: synthesized

<400> SEQUENCE: 35

Gly Asp Leu Val Thr Ser Thr Cys Leu Leu Gly Leu Cys Ala Glu Arg
1               5                   10                  15

Gly

<210> SEQ ID NO 36
<211> LENGTH: 17
<212> TYPE: PRT
<213> ORGANISM: Artificial
<220> FEATURE:
<223> OTHER INFORMATION: synthesized

<400> SEQUENCE: 36

Leu Ser Ala Gly Pro Leu Asp Trp Trp Ser Ser Leu Arg Ser Ser Ala
1               5                   10                  15

Ser

<210> SEQ ID NO 37
<211> LENGTH: 17
<212> TYPE: PRT
<213> ORGANISM: Artificial
<220> FEATURE:
<223> OTHER INFORMATION: synthesized

<400> SEQUENCE: 37

Leu Phe Ser Leu Leu Pro Ala Leu Ala Phe Leu Gly Glu Glu Gln Gly
1               5                   10                  15

Pro

<210> SEQ ID NO 38
<211> LENGTH: 17
<212> TYPE: PRT
<213> ORGANISM: Artificial
<220> FEATURE:
<223> OTHER INFORMATION: synthesized

<400> SEQUENCE: 38

Ala Asp Ser Phe Val Leu Ala Ser Ala Gly Ser Val Gln Val Val Val
1               5                   10                  15

Ala

<210> SEQ ID NO 39
<211> LENGTH: 19
<212> TYPE: PRT
<213> ORGANISM: Artificial
<220> FEATURE:
<223> OTHER INFORMATION: synthesized

<400> SEQUENCE: 39

Glu Gly Leu Val Ala Ser Val Ser Cys Tyr Ala Gly Gly Ser Cys Ala
1               5                   10                  15

Val Ser Arg

<210> SEQ ID NO 40
<211> LENGTH: 19
<212> TYPE: PRT
<213> ORGANISM: Artificial
```

```
<220> FEATURE:
<223> OTHER INFORMATION: synthesized

<400> SEQUENCE: 40

Ser Cys Asn Leu Pro Ala Cys Phe Asp Ile Leu Phe Arg Ser Leu Asp
1               5                   10                  15

Lys Trp Ser

<210> SEQ ID NO 41
<211> LENGTH: 17
<212> TYPE: PRT
<213> ORGANISM: Artificial
<220> FEATURE:
<223> OTHER INFORMATION: synthesized

<400> SEQUENCE: 41

Ser Cys Asn Arg Asp Tyr Asn Trp Leu Asp Ser Val Gly His Cys Val
1               5                   10                  15

Asn

<210> SEQ ID NO 42
<211> LENGTH: 19
<212> TYPE: PRT
<213> ORGANISM: Artificial
<220> FEATURE:
<223> OTHER INFORMATION: synthesized

<400> SEQUENCE: 42

Ser Cys Leu Gln Trp Ser Phe Ile Gly Ala Tyr Ser Ser Leu Ser Gly
1               5                   10                  15

Gln Pro Ser

<210> SEQ ID NO 43
<211> LENGTH: 19
<212> TYPE: PRT
<213> ORGANISM: Artificial
<220> FEATURE:
<223> OTHER INFORMATION: synthesized

<400> SEQUENCE: 43

Ser Cys Ser Leu Cys Val Leu Pro Ser Val Thr Phe Asp Leu Lys Leu
1               5                   10                  15

Glu Cys Cys

<210> SEQ ID NO 44
<211> LENGTH: 19
<212> TYPE: PRT
<213> ORGANISM: Artificial
<220> FEATURE:
<223> OTHER INFORMATION: synthesized

<400> SEQUENCE: 44

Ser Ser Arg Ile Ser Asp Tyr Val Gly Leu Ser Ala Cys Pro Gly Gly
1               5                   10                  15

Cys Ala Ser

<210> SEQ ID NO 45
<211> LENGTH: 19
<212> TYPE: PRT
<213> ORGANISM: Artificial
<220> FEATURE:
<223> OTHER INFORMATION: synthesized
```

-continued

```
<400> SEQUENCE: 45

Ser Cys Phe Cys Ala Ile Leu Ile Lys Ile Ile Val Phe Leu Ser Leu
1               5                   10                  15

Val Phe Ser

<210> SEQ ID NO 46
<211> LENGTH: 9
<212> TYPE: PRT
<213> ORGANISM: Artificial
<220> FEATURE:
<223> OTHER INFORMATION: synthesized

<400> SEQUENCE: 46

Cys Ser Thr Ala Leu Lys Trp Thr Cys
1               5

<210> SEQ ID NO 47
<211> LENGTH: 43
<212> TYPE: PRT
<213> ORGANISM: Artificial
<220> FEATURE:
<223> OTHER INFORMATION: synthesized
<220> FEATURE:
<221> NAME/KEY: MISC_FEATURE
<222> LOCATION: (1)..(1)
<223> OTHER INFORMATION: covalently coupled to linker
<220> FEATURE:
<221> NAME/KEY: MISC_FEATURE
<222> LOCATION: (20)..(20)
<223> OTHER INFORMATION: free C-terminal amino acid
<220> FEATURE:
<221> NAME/KEY: MISC_FEATURE
<222> LOCATION: (21)..(21)
<223> OTHER INFORMATION: free N-terminal amino acid
<220> FEATURE:
<221> NAME/KEY: MISC_FEATURE
<222> LOCATION: (43)..(43)
<223> OTHER INFORMATION: covalently coupled to linker

<400> SEQUENCE: 47

Ser Ser His Arg Thr Asn His Lys Lys Asn Asn Pro Lys Lys Lys Asn
1               5                   10                  15

Lys Thr Arg Gly Ser Ser Phe Tyr Gly Glu Val Gly Tyr Val Gly Ala
            20                  25                  30

Ser Leu Tyr Ala Gly Gly Ala Ser Ser Arg Gly
        35                  40

<210> SEQ ID NO 48
<211> LENGTH: 57
<212> TYPE: DNA
<213> ORGANISM: Artificial
<220> FEATURE:
<223> OTHER INFORMATION: synthesized

<400> SEQUENCE: 48
agcagccaca gaactaatca caagaagaat aatccgaaga agaagaataa gactaga        57

<210> SEQ ID NO 49
<211> LENGTH: 54
<212> TYPE: DNA
<213> ORGANISM: Artificial
<220> FEATURE:
<223> OTHER INFORMATION: synthesized
```

-continued

```
<400> SEQUENCE: 49
ttctacgggg aggttgggta cgttggagct agcttatacg ctgggggcgc ctcc       54

<210> SEQ ID NO 50
<211> LENGTH: 5
<212> TYPE: PRT
<213> ORGANISM: Artificial
<220> FEATURE:
<223> OTHER INFORMATION: synthesized

<400> SEQUENCE: 50

Gly Arg Glu Val Asp
1               5
```

COMPOSITIONS AND METHODS FOR PROMOTING ATTACHMENT OF CELLS OF ENDOTHELIAL CELL LINEAGE TO MEDICAL DEVICES

CROSS REFERENCE TO RELATED APPLICATIONS

This is a nonprovisional application which claims priority benefit of U.S. Provisional Application No. 60/758,029, filed 11 Jan. 2006; which is hereby incorporated by reference herein, and is related to International Application No. PCT/US2007/000517, filed 9 Jan. 2007; and U.S. application Ser. No. 11/649,950, filed 5 Jan. 2007, and International Application No. PCT/US2007/000518, filed 9 Jan. 2007.

FIELD OF THE INVENTION

The present invention relates to compositions and methods for promoting the attachment of cells of endothelial cell lineage to an intravascular device.

BACKGROUND OF THE INVENTION

Atherosclerosis causes stenosis and occlusion of arteries. Stenting and bypass surgery are often used to treat severe disease in small caliber arteries (defined as less than 6 mm in diameter). Arterial bypass procedures are limited by the availability of a vascular conduit, such as internal mammary artery or saphenous vein. Unfortunately, synthetic conduits made from polytetrafluoroethylene (PTFE) or polyethylene terephthalate (PET) suffer from unacceptably high rates of thrombosis in small caliber grafts due to their lack of an adherent, quiescent endothelium. Hence, developing a non-thrombogenic, small caliber arterial replacement has emerged as one of the most important goals of cardiovascular intervention in the elderly population.

Intravascular devices are placed within body vasculature; typically, at a site of occlusion in a vessel or the heart, or to replace or support a vessel or portion of the heart. Intravascular devices are normally manufactured from biologically inert materials intended to reduce the complications of insertion of a foreign object into the vasculature, such as stainless steel, titanium, polymers, or a combination thereof. However numerous problems have been reported to be associated with these devices, including thrombosis, neointima formation, and restenosis. Attempts have been made to reduce or eliminate the complications of intravascular devices. For example, to address the problem of thrombosis, an individual with an intravascular device may receive an anticoagulant and anti-platelet drugs, such as ticlopidin or aspirin.

One approach to overcome complications associated with intravascular devices is a strategy to promote rapid endothelialization of the surface of the device in contact with vasculature and/or blood. In that regard, U.S. Pat. No. 7,037,332 describes a medical device having a matrix coating made by cross-linking to the matrix an antibody having binding specificity for an endothelial cell antigen, for promoting attachment of endothelial cells to the medical device. U.S. Pat. No. 6,897,218 discloses metal complexes of a piperazine derivative, which are described as promoting re-endothelialization, but which do not appear to directly bind to a device, and appear to rely on large volumes of a blood-circulating composition to be effective. U.S. Pat. No. 6,140,127 describes a method of coating a stent by applying a polymer layer, applying pyridine and tresyl chloride, and applying a five amino acid peptide (glycine-arginine-glutamic acid-aspartic acid-valine; SEQ ID NO:50) for adhering cells to the stent. U.S. Pat. No. 5,929,060 discloses derivatives of the steroid DHEA, which are described as useful for re-endothelialization. U.S. Pat. No. 5,643,712 discloses coating of vessels of an organ or tissue to be grafted with a partially polymerized extracellular matrix preparation derived from endothelial cells, which may serve as a surface promoting re-endothelialization. Device design may be modified to promote the occurrence of re-endothelialization. U.S. Pat. No. 6,436,132 discloses an intraluminal prosthesis for treating a stenotic region in a blood vessel. The openings in the stent are said to allow for re-endothelialization of the blood vessel.

Cells of the endothelial cell lineage include endothelial cells and endothelial progenitor cells. Endothelial cells line all parts of the vasculature, where they regulate coagulation, inflammation, vascular permeability, and nutrient exchange between the blood and the interstitium. In areas where the endothelium is focally denuded, coagulation rapidly ensues. Focal coagulation of a blood vessel can lead to thrombosis and vascular occlusion, or other thromboembolic events. Endothelial progenitor cells have been shown to contribute to angiogenesis and vasculogenesis in a variety of model systems, and also to contribute to endothelialization of endovascular grafts in animal models. However, spontaneous endothelialization of endovascular grafts is rare in human patients, perhaps because the graft materials are engineered to resist molecular adhesion and coagulation, and endothelial progenitor cells have no ability to adhere, survive, and proliferate on such materials. Thus, there still remains a need for methods to promote endothelialization of intravascular devices such as by treating the devices so as to promote colonization and/or growth of nascent endothelium on the treated devices.

At least two types of endothelial progenitor cells can be isolated from peripheral blood: "early" endothelial progenitor cells, which live for 2 to 4 weeks in vitro and secrete potent angiogenic factors; and "late" endothelial progenitor cells, which grow out at 3 weeks and can replicate for up to 100 population doublings. Early endothelial progenitor cells are derived from bone marrow angioblasts under the influence of vascular endothelial growth factor (VEGF). Early endothelial progenitor cells have the phenotype CD133+/−, CD34+, VEGFR-2+, CD31+, vWF−, VE-cadherin−, E-selectin−, eNOS−, and telomerase+. Late endothelial progenitor cells have the phenotype CD133+/−, CD34+, VEGFR-2+, CD31+, vWF+, VE-cadherin+, E-selectin+, eNOS+, and telomerase+. Differentiated endothelial progenitor cells are similar to late endothelial progenitor cells, except that the former are CD133(−) and telomerase(−). Other endothelial progenitor cell subpopulations, and their phenotypic markers, are being described in the art.

Desired is an approach that can do one or more of attach, recruit, support, and differentiate a nascent layer of cells of endothelial cell lineage on an intravascular device surface. For example, it is desired to have an intravascular device with a coating capable of capturing circulating cells of an endothelial cell lineage so that they are seeded on the surface of an intravascular device, with the intended benefit of reducing the occurrence of complications associated with that type of intravascular device, such as one or more of thrombosis, neointima formation, and restenosis.

SUMMARY OF THE INVENTION

The present invention provides biofunctional coating compositions comprising at least one binding domain that specifically binds to a metallic surface of a medical device (for ease of reference, this binding domain is referred to herein as:

"surface-binding domain") which is coupled to at least one binding domain that specifically binds to cells of endothelial cell lineage (for ease of reference, this binding domain is referred to herein as: "endothelial-binding domain"); wherein the surface-binding domain and the endothelial-binding domain consist essentially of the amino acid sequences illustrated herein in Tables 1 and 3, respectively. The surface-binding domain and the endothelial cell-binding domain may be coupled together directly (e.g., during synthesis, or by chemical means) or may be coupled via a linker, to form a single molecule of the biofunctional coating composition of the present invention.

The present invention also provides surface-binding domains comprised of peptides consisting essentially of SEQ ID NOs:1-8; and polynucleotides encoding such surface-binding domains.

The present invention also provides endothelial-binding domains comprised of peptides consisting essentially of SEQ ID NOs:9-46; and polynucleotides encoding such endothelial-binding domains.

Using the compositions according to the present invention, the present invention also provides: methods for coating a metallic surface of a medical device so as to render the coated surface capable of adhering to cells of endothelial cell lineage (e.g., one or more of endothelial cells, and endothelial progenitor cells) when the coated surface is contacted by cells of endothelial cell lineage; methods for promoting adherence of cells of endothelial cell lineage to at least one metallic surface of a medical device; and methods for promoting endothelialization of at least one metallic surface of a medical device by coating the at least one surface to promote attachment of cells of the endothelial cell lineage. These methods comprise contacting the at least one metallic surface of the medical device to be coated with a biofunctional coating composition (also known as an "interfacial biomaterial") comprising at least one surface-binding domain of the present invention which is coupled to at least one endothelial-binding domain of the present invention. The biofunctional coating composition is contacted with and applied to at least one metallic surface of a medical device in forming a coating on the medical device, and wherein the at least one endothelial-binding domain is in an amount effective in the coating for adhering cells of endothelial cell lineage to, and preferably for promoting endothelialization of, the at least one coated surface of the medical device. The methods may further comprise the step of contacting the coated device with cells of endothelial cell lineage in promoting one or more of attachment, adherence, support for growth, and support for differentiation. This latter step may occur in vitro (e.g., attaching the endothelial cells prior to implantation of the device); or may occur in vivo (e.g., once implanted, the individual's endothelial cells migrate from adjacent arterial areas of intact endothelium to, or as circulating cells, come in contact with, and adhere to, the surface of the device coated by the biofunctional coating composition).

With respect to the methods and compositions according to the present invention, at least one endothelial-binding domain may comprise a single type (e.g., that binds specifically to a subset of cells of endothelial cell lineage; for example, to endothelial cells only; or with broad specificity (e.g., in general, for both endothelial cells and endothelial progenitor cells)), or may comprise multiple types (e.g., one type that binds specifically to endothelial cells; and another type that binds specifically to endothelial progenitor cells).

Using the compositions according to the present invention, the invention also relates to a method of promoting the adherence of cells of endothelial cell lineage to a medical device, and more preferably an intravascular device. Also provided is a method for manufacturing a medical device. These methods comprise contacting at least one metallic surface of a medical device with a biofunctional coating composition (which binds specifically to cells of endothelial cell lineage) in forming at least one coated metallic surface; and contacting the at least one coated surface with cells of endothelial cell lineage (e.g., in promoting adherence of cells of endothelial cell lineage to the at least one coated surface); wherein the biofunctional coating composition comprises at least one surface-binding domain and at least one endothelial-cell binding domain; and wherein the at least one surface-binding domain and the at least one endothelial-cell binding domain are coupled together. Contacting of cells of endothelial cell lineage with the biofunctional coating composition on the medical device can be by any method known in the art for promoting binding interactions between an affinity molecule and its ligand, such as, for example, incubating, dipping, spraying, or brushing a solution containing cells of endothelial cell lineage on the medical device comprising the biofunctional coating composition. Also provided is a medical device comprising a coating formed by applying an effective amount of the biofunctional coating composition to a metallic surface of the medical device, in rendering the medical device compatible for attachment of endothelial cells, and more preferably for the attachment of endothelial cells with subsequent endothelialization of the coated surface.

Alternatively, provided is a method for promoting endothelialization of a vascular device so that to a selected metallic surface of the device, once that surface is coated and the device implanted, promoted is attachment of cells of endothelial cell lineage. The method comprises the steps of: (a) contacting a biofunctional coating composition described herein to at least one metallic surface of a vascular device to be endothelialized, so that the biofunctional coating composition binds to the at least one metallic surface, in forming a coated metallic surface on the vascular device; wherein the biofunctional coating composition comprises at least one surface-binding domain having an amino acid sequence consisting essentially of SEQ ID NOs:1-8, coupled to at least one endothelial-cell binding domain having an amino acid sequence consisting essentially of SEQ ID NOs:9-46; and (b) implanting the device into an individual (human or non-human) in need of the device; wherein cells of endothelial cell lineage (produced by the individual) contact, attach and adhere to the coated surface of the device (primarily mediated by the cells binding to the at least one endothelial binding domain of the biofunctional coating composition), in promoting spread of cells of endothelial cell lineage over the coated metallic surface of the device, and in promoting endothelialization of the vascular device. Promoting endothelialization on the implanted device may further promote one or more of healing of tissue or vasculature adjacent to the implanted device, promote incorporation (integration) of the implanted device into the adjacent tissue, and reduce occurrence of thrombosis as related to the implanted device.

DETAILED DESCRIPTION OF THE INVENTION

The present invention provides compositions for an improved coating for medical devices, methods of coating medical devices using those compositions, and a metallic surface of a medical device which is coated with a biofunctional coating composition of the present invention.

Definition Section While the following terms are believed to be well understood by one of ordinary skill in the art, the following definitions are set forth to facilitate explanation of the invention.

The term "effective amount" is used herein, in referring to the biofunctional coating composition according to the present invention and for purposes of the specification and claims, to mean an amount sufficient of the biofunctional coating composition is applied to the at least one metallic surface to be coated (via contact of the at least one surface to the biofunctional coating) so as to (a) mediate binding of the biofunctional coating composition to the at least one metallic surface of the medical device in forming a coating; and (b) promote adherence of endothelial cells to, and more preferably, endothelialization of, the coated surface.

The term "cells of endothelial cell lineage" is used herein for purposes of the specification and claims, to mean endothelial cells at any development stage (e.g., ranging from early stages of development, such as an endothelial stem cell or progenitor cell, to a mature stage of development such as a fully differentiated, tissue specific endothelial cell); and including stem cells capable of differentiating into endothelial progenitor cells and/or endothelial cells, such stem cells sharing at least one surface molecule or receptor in common with endothelial cells (e.g., bone marrow angioblast; a cardiac Sca-1+ stem cell (which can be differentiated into endothelial cells in the presence of leukemia inhibitory factor (LIF)), an adipose-derived stem cell); or a combination thereof. Thus, cells of endothelial cell lineage include endothelial cells, endothelial progenitor cells, and stem cells capable of differentiating into endothelial cells and/or endothelial progenitor cells. A preferred cell of endothelial cell lineage may be used in accordance with the present invention to the exclusion of a cell of endothelial cell lineage other than the preferred cell of endothelial cell lineage.

The term "endothelialization" is used herein unless otherwise specified, for purposes of the specification and claims, to mean one or more of the growth (desirably including proliferation) of endothelial cells, and differentiation of endothelial cells, on and over the at least one metallic surface of a medical device coated by an effective amount of the biofunctional coating composition according to the present invention. Preferably, once the cells of endothelial cell lineage are attached to the surface of a medical device coated by an effective amount of the biofunctional coating composition, promoted will be endothelial cell growth and development to provide an endothelial tissue layer. Thus, the term "endothelialization" can mean re-endothelialization of a vascular graft which has lost or been stripped of its endothelium due to any biological or mechanical process; or it may comprise growing new endothelial cells to cover a metallic surface of an implanted or implantable graft, or implanted or implantable medical device, which had not been previously covered by endothelial cells.

The term "medical device' is used herein, for purposes of the specification and claims, to refer to an intravascular device, vascular device, vascular graft, a lead or lead tip exposed to the vascular system (e.g., from a cardiac pacemaker or cardiac defribillator). In a preferred embodiment, within the scope and meaning of "medical device" herein is a device comprising a stent (as known in the art, a stent being a metallic and/or polymeric cage-like or tubular support device that is used to hold vessels (e.g., blood vessels) open). The terms "intravascular device" and "vascular device" are used interchangeably herein, for purpose of the specification and claims, to refer to a structure that is introduced into a human or animal vasculature to restore function of damaged, diseased, or blocked tissue, and includes prosthetic devices, and vascular grafts. In a preferred embodiment, within the scope and meaning of "intravascular device" or "vascular device" herein is a device comprising a stent. The term "vascular device" as used herein also includes device-related materials that are associated with the device and are also introduced into a human or animal body in conjunction with the device. Representative vascular devices include, but are not limited to, heart patches, artificial heart valves, annuloplasty rings, annular rings, mechanical assist devices, vascular sealing devices, central venous catheters, arterial catheters, pacemakers, defibrillators, guidewires, embolic protection filters, embolic devices (e.g., coils), implantable infusion pumps, and vascular sutures. Vascular grafts include coronary artery bypass grafts, prosthetic heart valves, peripheral vascular bypass grafts, vascular access grafts, and synthetic grafts. A preferred medical device may be used in accordance with the present invention to the exclusion of a medical device other than the preferred medical device.

A medical device may be comprised of, and hence have one or more surfaces comprised of, a variety of materials including, but not limited to, a metal, a metal oxide, a non-metal oxide, a ceramic, a rubber, a plastic, an acrylic, a silicone, a polymer, and combinations thereof. An intravascular device can be produced using any biocompatible material; however, because of the difficulties with biocompatibilities in the vasculature, it is preferred that the biocompatible material be relatively inert. Such devices are made of a variety of materials that are known in the art, but most typically are biologically inert polymers or metals. Metals used in the manufacture of medical devices are known in the art to include, without limitation, stainless steel, tantalum, gold, platinum, silver, tungsten, titanium, titanium alloys (for example, memory titanium alloys such as nitinol), a transition metal, alkali metals, and alkaline earth metals (each of the latter three comprise metals related in structure and function, as classified in the Periodic Table). Metal alloys (e.g., cobalt-chrome alloy) and metal oxides of each of these groups, individually and separately, are included. In the present invention, a preferred surface material to which the biofunctional coating composition of the present invention becomes bound is a metal, and more preferably stainless steel. A preferred surface material of a medical device may be used in accordance with the present invention to the exclusion of a surface material of the medical device other than the preferred surface material.

When the term "surface" is used herein in conjunction with a medical device, generally it is referring to one or more metallic surfaces of the medical device which is or becomes exposed to biological solutions and/or biological tissue, and preferably comes in contact with blood and/or is introduced into vasculature of an individual; and hence, such surface is susceptible to any one or more of thrombosis, neointima formation, restenosis. "Metallic surface" means a surface material comprised of one or more of a metal, metal alloy, metal oxide, and a combination thereof.

The term "individual", as used herein, for purposes of the specification and claims, refers to either a human or an animal.

The term "vascular biologic", as used herein, refers to a biological substance which has specific biologic utility in one or more of: the repair or integration of a vascular device within the vascular system, especially after surgery or upon implantation of an intravascular device; and promotion of endothelialization. A vascular biologic may comprise a biological substance selected from the group consisting of a collagen (e.g., type IV and/or type V), vitrogen, laminin, entactin, fibronectin, glycans (e.g., proteoglycans, glycosaminoglycans), one or more growth factors supporting endothelial cell growth (e.g., vascular endothelial cell growth factor (VEGF), epidermal growth factor (EGF), fibroblast growth factor (basic fibroblast growth factor (bFGF), acidic fibroblast growth factor (aFGF)), heparin-binding epidermal-like growth factor, angiopoietin 1 (ang-1), angiopoietin 2 (ang-2), hepatocyte growth factor (HGF), platelet-derived endothelial cell growth factor (PD-ECGF), LIF), angiopoietins (e.g., ang-3, ang-4) and a combination thereof. A preferred vascular biologic may be used in accordance with the present invention to the exclusion of a vascular biologic other than the preferred vascular biologic.

The term "surface-binding domain", used herein for purposes of the specification and claims, refers to a peptide that binds specifically to a metallic surface of a medical device; and more particularly, has binding specificity for stainless steel of a stent, and consists essentially of an amino acid sequence selected from the group consisting of SEQ ID NOs: 1-8 (see, also, Table 1). A preferred surface-binding domain (including the type of surface to which it binds with specificity) may be used with the present invention to the exclusion of a surface-binding domain other than the preferred surface-binding domain. The surface-binding domain in the biofunctional coating composition of the present invention is selected to specifically bind (e.g., typically, noncovalently, ionically, or electrostatically) to the metallic material of at least one surface of the medical device desired to be coated, wherein generally, such at least one surface becomes exposed to a biological tissue and/or biological fluid associated with vasculature when the medical device is implanted in an individual in need of the medical device.

The term "time sufficient for binding" generally refers to a temporal duration sufficient for specific binding of a binding domain described herein, and a substrate for which the binding domain has binding specificity, as known to those skilled in the art.

The term "endothelial-binding domain", used herein for purposes of the specification and claims, refers to a peptide that specifically binds to one or more cells of endothelial cell lineage, and wherein the peptide consists essentially of an amino acid sequence selected from the group consisting of SEQ ID NOs:9-46 (see, also, Table 3). Such an endothelial-cell binding domain may specifically bind to a specific type of cell of endothelial cell lineage (e.g., endothelial cells, or endothelial progenitor cell, or endothelial cells of a specific tissue origin (e.g., cardiac endothelial cells)), or to more than one type of cells of endothelial cell lineage (e.g., sharing a common surface molecule bound by the endothelial cell-binding domain). Alternately, the biofunctional coating compositions of the present invention may be comprised of more than one type of endothelial-binding domain (e.g., two or more different peptides, each with binding specificity for different cells of endothelial cell lineage). Thus, in such case, each type of endothelial-binding domain has a binding specificity for cells of endothelial cell lineage that differs from the binding specificity of another type of endothelial-binding domain present in the biofunctional coating composition. Excluded from the definition "endothelial-binding domain" is an antibody, and more particularly an antibody having binding specificity for endothelial cells. A preferred endothelial-binding domain (including the type of cells of endothelial cell lineage to which it binds with specificity) may be used in accordance with the present invention to the exclusion of an endothelial-binding domain other than the preferred endothelial-binding domain. Thus, preferred endothelial-binding domain peptides consisting essentially of amino acid sequences selected from the group consisting of SEQ ID NOs:9-46, and excluded are endothelial-binding domain peptides consisting essentially of amino acid sequences other than those selected from the group consisting of SEQ ID NOs:9-46.

The terms "biofunctional coating composition" and "interfacial biomaterial" are used interchangeably, in reference to the present invention and for purposes of the specification and claims, to refer to a composition comprising at least one surface-binding domain comprising a peptide consisting essentially of an amino acid sequence selected from the group consisting of SEQ ID NOs:1-8, and at least one endothelial-binding domain comprising a peptide consisting essentially of an amino acid sequence selected from the group consisting of SEQ ID NOs:9-46, wherein the at least one surface-binding domain and at least one endothelial-binding domain are coupled together (e.g., by one or more of physically, chemically, synthetically, or biologically (e.g., via recombinant expression)) in such a way that each binding domain retains its respective function to bind to the respective molecule for which it has binding specificity (as described herein). Such coupling may include a multimeric molecule having two or more surface-binding domains coupled together, wherein an endothelial-binding domain is coupled to all or only some of the surface-binding domains of the multimeric molecule. For example, using standard reagents and methods known in the art of peptide chemistry, two binding domains may be coupled via a side chain-to-side chain bond (e.g., where each of the peptides have a side chain amine (e.g., such as the epsilon amine of lysine)), a side chain-to-N terminal bond (e.g., coupling the N-terminal amine of one peptide with the side chain amine of the other peptide), a side chain-to-C-terminal bond (e.g., coupling the C-terminal chemical moiety (e.g., carboxyl) of one peptide with the side chain amine of the other peptide), an N-terminal-to-N-terminal bond, an N-terminal to C-terminal bond, a C-terminal to C-terminal bond, or a combination thereof. In synthetic or recombinant expression, a peptide of a surface-binding domain can be coupled directly to a peptide of an endothelial-binding domain by synthesizing or expressing both peptides as a single peptide. The coupling of surface-binding domain to an endothelial-binding domain may also be via a linker to form a biofunctional coating composition.

The biofunctional coating composition or interfacial biomaterial of the present invention comprises: (a) the at least one surface-binding domain according to the present invention, in an amount effective to mediate the binding of the biofunctional coating composition or interfacial biomaterial to the metallic surface material of the medical device for which the at least one surface-binding domain has binding specificity; and (b) the at least one endothelial-binding domain according to the present invention in an amount effective to confer to the coated medical device the ability to attach or adhere to cells of endothelial cell lineage, and more preferably and additionally, to promote endothelialization of the coated surface of the medical device; wherein the at least one surface-binding domain and the at least one endothelial-binding domain are coupled together. In a preferred embodiment, a linker is used to join together the at least one surface-binding domain and the at least one endothelial-binding domain.

In function, when the biofunctional coating composition is applied to a metallic surface of a medical device (by contacting the biofunctional coating composition with the metal), binding of the biofunctional coating composition to the metallic surface is mediated primarily by a domain of the biofunctional coating composition comprising the at least one surface-binding domain according to the present invention; and the properties of, or associated with, the biofunctional coating composition as related to attachment, adherence, endothelialization, or a combination thereof, are mediated primarily by a domain of the biofunctional coating composition comprising the at least one endothelial-binding domain according to the present invention. Thus, when a medical device is coated with a biofunctional coating composition of the present invention, and then the coated medical device is introduced into or applied to an individual, the biofunctional coating composition is then the interface (hence, "interfacial biomaterial") between the medical device and the biological tissues and/or biological fluids of the individual. Accordingly, provided is a method of promoting the attachment and adherence of cells of endothelial cell lineage to a medical device, the method comprising coating one or more metallic surfaces of the medical device with a biofunctional coating composition or interfacial biomaterial comprising at least one surface-binding domain according to the present invention and at least one endothelial-binding domain according to the present invention, wherein the at least one surface-binding domain and the at least one endothelial binding domain are coupled together. In another embodiment, provided is a method of promoting endothelialization on a metallic surface of a medical device, the metallic surface being suitable for contacting one or more of a biological tissue (e.g., a blood vessel) or biological fluid (e.g., blood) associated with vasculature, the method comprising coating one or more metallic surfaces of the medical device with a biofunctional coating composition or interfacial biomaterial comprising at least one surface-binding domain according to the present invention and at least one endothelial-binding domain according to the present invention, wherein the at least one surface-binding domain and the at least one endothelial-binding domain are coupled together, and wherein the at least one endothelial-binding domain is bound to cells of endothelial cell lineage.

The term "linker" is used, for purposes of the specification and claims, to refer to a compound or moiety that acts as a molecular bridge to couple at least two different molecules (e.g., with respect to the present invention, coupling a surface-binding domain to an endothelial-binding domain, or coupling two or more surface-binding domains in making a multimeric molecule comprised of two or more surface-binding domains, or coupling two or more endothelial-binding domains in making a multimeric molecule comprised of two or more endothelial-binding domains). Thus, for example, one portion of the linker binds to a surface-binding domain according to the present invention, and another portion of the linker binds to an endothelial-binding domain according to the present invention. As known to those skilled in the art, and using methods known in the art, a surface-binding domain and an endothelial-binding domain may be coupled to the linker in a step-wise manner, or may be coupled simultaneously to the linker, to form a biofunctional coating composition or interfacial biomaterial according to the present invention. There is no particular size or content limitations for the linker so long as it can fulfill its purpose as a molecular bridge, and that the binding specificities of the biofunctional coating composition are substantially retained.

Linkers are known to those skilled in the art to include, but are not limited to, chemical chains, chemical compounds (e.g., reagents), and the like. The linkers may include, but are not limited to, homobifunctional linkers and heterobifunctional linkers. Heterobifunctional linkers, well known to those skilled in the art, contain one end having a first reactive functionality (or chemical moiety) to specifically link a first molecule, and an opposite end having a second reactive functionality to specifically link to a second molecule. It will be evident to those skilled in the art that a variety of bifunctional or polyfunctional reagents, both homo- and hetero-functional (such as those described in the catalog of the Pierce Chemical Co., Rockford, Ill.), amino acid linkers (typically, a short peptide of between 3 and 15 amino acids, and often containing amino acids such as glycine, and/or serine), and polymers (e.g., polyethylene glycol) may be employed as a linker with respect to the present invention. In one embodiment, representative peptide linkers comprise multiple reactive sites to be coupled to a binding domain (e.g., polylysines, polyornithines, polycysteines, polyglutamic acid and polyaspartic acid) or comprise substantially inert peptide linkers (e.g., lipolyglycine, polyserine, polyproline, polyalanine, and other oligopeptides comprising alanyl, serinyl, prolinyl, or glycinyl amino acid residues). In some embodiments wherein amino acid linker is chosen, the biofunctional coating composition of the present invention may be synthesized to be a single, contiguous peptide comprising a surface-binding domain, a linker, and an endothelial-binding domain. Thus, the linker attachment is simply via the bonds of the single contiguous peptide.

Suitable polymeric linkers are known in the art, and can comprise a synthetic polymer or a natural polymer. Representative synthetic polymers include but are not limited to polyethers (e.g., poly(ethylene glycol) ("PEG")), polyesters (e.g., polylactic acid (PLA) and polyglycolic acid (PGA)), polyamines, polyamides (e.g., nylon), polyurethanes, polymethacrylates (e.g., polymethylmethacrylate; PMMA), polyacrylic acids, polystyrenes, polyhexanoic acid, flexible chelators such as EDTA, EGTA, and other synthetic polymers which preferably have a molecular weight of about 20 daltons to about 1,000 kilodaltons. Representative natural polymers include but are not limited to hyaluronic acid, alginate, chondroitin sulfate, fibrinogen, fibronectin, albumin, collagen, calmodulin, and other natural polymers which preferably have a molecular weight of about 200 daltons to about 20,000 kilodaltons (for the constituent monomers). Polymeric linkers can comprise a diblock polymer, a multi-block copolymer, a comb polymer, a star polymer, a dendritic or branched polymer, a hybrid linear-dendritic polymer, a branched chain comprised of lysine, or a random copolymer. A linker can also comprise a mercapto(amido)carboxylic acid, an acrylamidocarboxylic acid, an acrlyamido- amidotriethylene glycolic acid, 7-aminobenzoic acid, and derivatives thereof. Linkers are known in the art and include linkers that can be cleaved, and linkers that can be made reactive toward other molecular moieties or toward themselves, for cross-linking purposes.

Depending on such factors as the molecules to be linked, and the conditions in which the linking is performed, the linker may vary in length and composition for optimizing such properties as preservation of biological function, stability, resistance to certain chemical and/or temperature parameters, and of sufficient stereo-selectivity or size. For example, the linker should not significantly interfere with the ability of a surface-binding domain to function in a biofunctional coating composition (i.e., to sufficiently bind, with appropriate avidity for the purpose, to a surface for a medical device for which it has specificity according to the present invention). Likewise, the linker should not significantly interfere with the ability of an endothelial-binding domain to function in a biofunctional coating composition (i.e., to sufficiently bind, with appropriate avidity for the purpose, to cells of endothelial cell lineage for which it has specificity according to the present invention). A preferred linker may be a molecule which may have activities which enhance or complement the effect of the biofunctional coating composition of the present invention. For example, using polyethylene glycol or other polymeric molecule or protein (e.g., albumin) as a linker may serve to help prevent non-specific protein and/or undesired cell adherence to the surface of the medical device coated with a biofunctional coating composition according to the present invention. A preferred linker may be used in the present invention to the exclusion of a linker other than the preferred linker.

The terms "binds specifically" or "binding specificity", and like terms used herein, are interchangeably used, for the purposes of the specification and claims, to refer to the ability of a binding domain (as described herein) to have a binding affinity that is greater for one target molecule or surface material selected to be bound (the latter, "target surface material") over another molecule or surface material (other than the target molecule or target surface material); e.g., an affinity for a given substrate in a heterogeneous population of other substrates which is greater than, for example, that attributable to non-specific adsorption. For example, a surface-binding domain has binding specificity for a metallic surface, and more preferably a stainless steel surface, of a medical device, when the surface-binding domain demonstrates preferential binding to metal, as compared to binding to another component or material of the medical device (such as a polymer). Such preferential binding may be dependent upon the presence of a particular conformation, structure, and/or charge on or within the molecule or material for which the binding domain has binding specificity, such that it recognizes and binds to that molecule or material rather than to molecules or materials in general.

In some embodiments, a binding domain that binds specifically to a particular surface, material or composition binds at least 10%, 20%, 30%, 40%, 50%, 60%, 70%, 80%, 90%, 100%, 200%, 300%, 400%, 500%, or a higher percentage, than the binding domain binds to an appropriate control such as, for example, a different material or surface, or a protein typically used for such comparisons such as bovine serum albumin. For example, binding specificity can determined by an assay in which quantitated is a signal (e.g., fluorescence, or colorimetric) representing the relative amount of binding between a peptide and target cells, as compared to peptide and non-target cells. Thus, if in such an assay, the results indicate that about 40% of the endothelial cells (as target cells) present in the assay are bound by a peptide, and less than 10% of the other cells (e.g., smooth muscle cells; "non-target cells") present in the assay are bound by the peptide, then the peptide is said to have binding specificity for endothelial cells. In a preferred embodiment, the binding domain has binding specificity that is additionally characterized by an EC50 of 10 µM or less, and more preferably less than 1 µM. The EC50 can be determined using any number of methods known in the art, such as by generating a concentration response curve from a binding assay in which the concentration of the peptide is titered with a known amount of material or cells for which the peptide has binding specificity (see, for example, methods described in Examples 2 and 3 herein). In such case, the EC50 represents the concentration of peptide producing 50% of the maximal binding observed for that peptide in the assay.

The term "peptide" is used herein, for the purposes of the specification and claims to refer to an amino acid chain of no less than about 3 amino acids and no more than about 500 amino acid residues in length, wherein the amino acid chain may include naturally occurring amino acids, synthetic amino acids, genetically encoded amino acids, non-genetically encoded amino acids, and combinations thereof; however, specifically excluded from the scope and definition of "peptide" herein is an antibody. Preferably, the peptide comprising a binding domain according to the present invention comprises a contiguous sequence of no less than 7 amino acids and no more than about 60 amino acids in length. A peptide used in accordance with the present invention may be produced by chemical synthesis, recombinant expression, biochemical or enzymatic fragmentation of a larger molecule, chemical cleavage of larger molecule, a combination of the foregoing or, in general, made by any other method in the art, and preferably isolated. The term "isolated" means that the peptide is substantially free of components which have not become part of the integral structure of the peptide itself; e.g., such as substantially free of cellular material or culture medium when produced by recombinant techniques, or substantially free of chemical precursors or other chemicals when chemically synthesized or produced using biochemical or chemical processes. A preferred peptide may be used in the present invention to the exclusion of a peptide other than the preferred peptide.

Peptides can include L-form amino acids, D-form amino acids, or a combination thereof. Representative non-genetically encoded amino acids include but are not limited to 2-aminoadipic acid; 3-aminoadipic acid; β-aminopropionic acid; 2-aminobutyric acid; 4-aminobutyric acid (piperidinic acid); 6-aminocaproic acid; 2-aminoheptanoic acid; 2-aminoisobutyric acid; 3-aminoisobutyric acid; 2-aminopimelic acid; 2,4-diaminobutyric acid; desmosine; 2,2'-diaminopimelic acid; 2,3-diaminopropionic acid; N-ethylglycine; N-ethylasparagine; hydroxylysine; allo-hydroxylysine; 3-hydroxyproline; 4-hydroxyproline; isodesmosine; allo-isoleucine; N-methylglycine (sarcosine); N-methylisoleucine; N-methylvaline; norvaline; norleucine; ornithine; and 3-(3,4-dihydroxyphenyl)-L-alanine ("DOPA"). Representative derivatized amino acids include, for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups can be derivatized to form salts, methyl and ethyl esters or other types of esters or hydrazides. Free hydroxyl groups can be derivatized to form O-acyl or O-alkyl derivatives. The imidazole nitrogen of histidine can be derivatized to form N-im-benzylhistidine. In a preferred embodiment, and in a biofunctional coating composition according to the present invention, the at least one surface-binding domain comprises an N-terminal amino acid, a C-terminal amino acid, or a combination thereof, wherein such amino acid is a non-genetically encoded amino acid that enhances the binding avidity (strength of binding interactions) of the surface-binding domain to the surface of a medical device for which it has binding specificity. Such amino acids can be incorporated into a peptide comprising a surface-binding domain by standard methods known in the art for solid phase and/or solution phase synthesis. For example, in one embodiment, from about one to about four residues of DOPA, a hydroxy-amino acid (e.g., one or more of hydroxylysine, allo-hydroxylysine, hydroxyproline, and the like) or a combination thereof, is added as terminal amino acids of an amino acid sequence of a peptide during synthesis, wherein the peptide comprises a surface-binding domain used in the biofunctional coating composition according to the present invention for enhancing the strength of the binding interactions (e.g., via electrostatic or ionic interactions) between the biofunctional coating composition and the at least one metallic surface of the medical device to be coated.

A peptide according to the present invention may be modified, such as by addition of chemical moieties, or substitutions, insertions, and deletions of amino acids, where such modifications provide for certain advantages in its use; provided the peptide consists essentially of an amino acid sequence illustrated in any one of SEQ ID NOs:1-47. When used herein in reference to the present invention and for purposes of the specification and claims, the terminology "consisting essentially of" or like terms (e.g., "consists essentially of") refers to a peptide which includes the amino acid sequence of the peptides described herein or a peptide having at least 70% identity (and preferably at least 90% identity) thereto (as described in more detail herein), and may include additional amino acids at the carboxyl and/or amino terminal ends (e.g., from about 1 to about 20 amino acids per terminus), and which maintains the primary activity of the peptides as a binding domain described herein. In one example, a peptide consisting essentially of an amino acid sequence of SEQ ID NO:3 includes an amino acid sequence of SEQ ID NO:1 (the latter differing by having an additional 20 amino acids at the N-terminus, yet retaining the binding specificity for a metal surface; see e.g., Example 2 and Table 2). In another non-limiting example, an endothelial-binding domain comprising a peptide "consisting essentially of" any one of the amino acid sequences illustrated as SEQ ID NOs: 9-46 will possess the activity of binding cells of endothelial cell lineage with binding specificity, as provided herein; and will not possess any characteristics which constitutes a material change to the basic and novel characteristics of the peptide as an endothelial-binding domain (e.g., thus, in the foregoing example, a full length naturally occurring polypeptide, or a genetically engineered polypeptide, which has a primary activity other than as a binding domain described herein, and which contains the amino acid sequence of a binding domain comprising a peptide described in the present invention, would not constitute a peptide "consisting essentially of" a peptide or amino acid sequence described in the present invention).

Thus, the term "peptide" encompasses any of a variety of forms of peptide derivatives including, for example, amides, conjugates with proteins, cyclone peptides, polymerized peptides, conservatively substituted variants, analogs, fragments, chemically modified peptides, and peptide mimetics. Any peptide derivative that has desired binding characteristics of a binding domain according to the present invention can be used in the practice of the present invention. For example, a chemical group, added to the N-terminal amino acid of a peptide to block chemical reactivity of that amino terminus of the peptide, comprises an N-terminal group. Such N-terminal groups for protecting the amino terminus of a peptide are well known in the art, and include, but are not limited to, lower alkanoyl groups, acyl groups, sulfonyl groups, and carbamate forming groups. Preferred N-terminal groups may include acetyl, Fmoc, and Boc. A chemical group, added to the C-terminal amino acid of a synthetic peptide to block chemical reactivity of that carboxy terminus of the peptide, comprises a C-terminal group. Such C-terminal groups for protecting the carboxy terminus of a peptide are well known in the art, and include, but are not limited to, an ester or amide group. Terminal modifications of a peptide are often useful to reduce susceptibility by proteinase digestion, and to therefore prolong a half-life of peptides in the presence of biological fluids where proteases can be present. Optionally, a peptide comprising a binding domain, as described herein, can comprise one or more amino acids that have been modified to contain one or more chemical groups (e.g., reactive functionalities such as fluorine, bromine, or iodine) to facilitate linking the peptide to a linker molecule. As used herein, the term "peptide" also encompasses a peptide wherein one or more of the peptide bonds are replaced by pseudopeptide bonds including but not limited to a carba bond ($CH_2$—$CH_2$), a depsi bond (CO—O), a hydroxyethylene bond (CHOH—$CH_2$), a ketomethylene bond (CO—$CH_2$), a methylene-oxy bond ($CH_2$—O), a reduced bond ($CH_2$—NH), a thiomethylene bond ($CH_2$—S), an N-modified bond (—NRCO—), and a thiopeptide bond (CS—NH).

Peptides which are useful as binding domains in a biofunctional coating composition or method of using the biofunctional coating composition according to the present invention also include peptides having one or more substitutions, additions and/or deletions of residues relative to the sequence of an exemplary peptide disclosed in any one or more of Tables 1 and 3 and SEQ ID NOs:1-47 herein, so long as the binding properties of the original exemplary peptide are substantially retained. Thus, binding domain according to the present invention includes peptides that differ from the exemplary sequences disclosed herein by, for example, between about 1% to about 25% of the amino acid sequence of an exemplary peptide; yet substantially retain the ability of the corresponding exemplary sequence to bind to a particular material or to act as a binding domain with binding specificity as described herein (e.g., retains at least 50%, 75%, 100% or more of the binding specificity of an exemplary sequence disclosed herein, as measured using an appropriate assay). That is, binding domains according to the present invention preferably include peptides that share sequence identity with the exemplary sequences disclosed herein in the range of at least 50% to about 99% or greater sequence identity. Sequence identity may be calculated manually or it may be calculated using a computer implementation of a mathematical algorithm, for example, GAP, BESTFIT, BLAST, FASTA, and TFASTA, or other programs or methods known in the art. Alignments using these programs can be performed using the default parameters.

For example, consider surface-binding domains comprising a peptide consisting essentially of amino acid sequences identified in Table 1 as SEQ ID NOs:3 and 4. A consensus sequence may be written (using standard single letter amino acid designations) as a peptide consisting essentially of the amino acid sequence illustrated as SEQ ID NO:5. Thus, these amino acid sequences (SEQ ID NOs:3 and 4) share significant sequence homology (as described herein), but share sequence identity that is less than about 50%, yet substantially retain binding specificity for metals, particularly stainless steel.

A peptide having an amino acid sequence substantially identical to a sequence of an exemplary peptide disclosed herein may have one or more different amino acid residues as a result of substituting an amino acid residue in the sequence of the exemplary peptide with a functionally similar amino acid residue (a "conservative substitution"); provided that peptide containing a conservative substitution will substantially retain the binding specificity of the exemplary peptide not containing the conservative substitution. Examples of conservative substitutions include the substitution of one non-polar (hydrophobic) residue such as isoleucine, valine, leucine or methionine for another; the substitution of one aromatic residue such as tryptophan, tyrosine, or phenylalanine for another; the substitution of one polar (hydrophilic) residue for another such as between arginine and lysine, between glutamine and asparagine, between threonine and serine; the substitution of one basic residue such as lysine, arginine or histidine for another; or the substitution of one acidic residue such as aspartic acid or glutamic acid for another.

In yet another embodiment of the present invention, a binding domain may be described herein as comprising a peptide consisting essentially of a peptide (and/or its amino acid sequence) useful in the present invention.

[End of Formal Definition Section]

The present invention provides for a biofunctional coating composition (or interfacial biomaterial), peptides comprising endothelial-binding domains, peptides comprising surface-binding domains, methods for coating a medical device, methods for manufacturing of a medical device, and a coated medical device; all relating to a biofunctional coating composition comprising: at least one surface-binding domain comprising a peptide consisting essentially of an amino acid sequence selected from the group consisting of SEQ ID NOs: 1-8, and a combination thereof; and at least one endothelial-binding domain comprising a peptide consisting essentially of an amino acid sequence selected from the group consisting of SEQ ID NOs:9-46, and a combination thereof; wherein the at least one surface-binding domain is coupled to at least one endothelial-binding domain. The at least one surface-binding domain is in an amount effective to mediate the binding of the biofunctional coating composition to the selected metallic surface of the medical device for which the at least one surface-binding domain has binding specificity; and the at least endothelial-binding domain is in an amount effective to render a surface of the medical device coated by a biofunctional coating composition according to the present invention capable of promoting one or more of attachment to, adherence of, and endothelialization with, cells of endothelial cell lineage. The present invention is illustrated in the following examples, which are not intended to be limiting.

EXAMPLE 1

Illustrated in this example are various methods for producing a surface-binding domain and a endothelial-binding domain for the biofunctional coating compositions according to the present invention. Many of the peptides comprising the binding domains in the biofunctional coating composition according to the present invention (i.e., a surface-binding domain and an endothelial-binding domain) were developed using phage display technology.

Phage display technology is well-known in the art, and can be used to identify additional peptides for use as binding domains in the interfacial binding materials according to the present invention. In general, using phage display, a library of diverse peptides can be presented to a target substrate, and peptides that specifically bind to the substrate can be selected for use as binding domains. Multiple serial rounds of selection, called "panning," may be used. As is known in the art, any one of a variety of libraries and panning methods can be employed to identify a binding domain that is useful in a biofunctional coating composition according to the present invention. Panning methods can include, for example, solution phase screening, solid phase screening, or cell-based screening. Once a candidate binding domain is identified, directed or random mutagenesis of the sequence may be used to optimize the binding properties (including one or more of specificity and avidity) of the binding domain.

For example, a variety of different phage display libraries were screened for peptides that bind to a selected target substrate (e.g., a substrate selected to find a binding domain useful in the present invention). The substrate was either bound to or placed in (depending on the selected substrate) the wells of a 96 well microtiter plate. Nonspecific binding sites on the well surface of the polystyrene microtiter plate were blocked with a buffer containing 1% bovine serum albumin after overnight incubation at 4° C. The wells were then washed 5 times with a buffer containing phosphate buffered saline with Tween™ 20 ("PBS-T"). Each library was diluted in PBS-T and added at a concentration of $10^{10}$ pfu/ml in a total volume of 100 μl. After 3 hour of incubation at room temperature with shaking at 50 rpm, unbound phage were removed by multiple washes with PBS-T. Bound phage were recovered by denaturation with 0.1 M glycine buffer, pH2.2. The eluted phage were neutralized with phosphate buffer, and then added to E. coli cells in growth media. The cell and phage-containing media was cultured by incubation overnight at 37° C. in a shaker at 200 rpm. Phage-containing supernatant was harvested from the culture after centrifuging the culture. Second and third rounds of selection were performed in a similar manner to that of the first round of selection, using the amplified phage from the previous round as input. To detect phage that specifically bind to the selected substrate, enzyme-linked immunosorbent (ELISA-type) assays were performed using an anti-phage antibody conjugated to a detector molecule, followed by the detection and quantitation of the amount of detector molecule bound in the assay. The DNA sequences encoding peptides from the phage that specifically bind to the selected substrate were then determined; i.e., the sequence encoding the peptide is located as an insert in the phage genome, and can be sequenced to yield the corresponding amino acid sequence displayed on the phage surface.

As known to those skilled in the art and methods known in the art, peptides comprising the binding domains according to the present invention may be synthesized by any method for peptide synthesis including, but not limited to, solid phase synthesis, solution phase synthesis, and a combination thereof. For example, peptides comprising binding domains useful in the present invention were synthesized on a peptide synthesizer using standard solid-phase synthesis techniques, and using standard FMOC peptide chemistry. After all residues were coupled, simultaneous cleavage and side chain deprotection was performed using standard methods and reagents known in the art. After cleavage from the resin, the peptides were precipitated, and the precipitate was lyophilized. The peptides were then purified using reverse-phase high performance liquid chromatography; and peptide identity was confirmed with mass spectrometry.

EXAMPLE 2

This example illustrates the discovery and characterization of surface-binding domains comprising peptides having binding specificity for a metallic surface of a medical device, such as a stainless steel surface of a stent.

A. Phage Screening and Selections.

As a specific illustrative example, nonspecific binding sites in wells containing stainless steel stent material in polystyrene microtiter plates were blocked with a buffer containing 1% bovine serum albumin for 2 hours at room temperature. The wells and stainless steel stent material were then washed three times with PBS-T. The plate was incubated for 1 hour at room temperature with shaking at 50 rpm. Each of 17 different phage display libraries was diluted in PBS+1% BSA and was added at a concentration of $10^{10}$ pfu/ml in a total volume of 250 μl. After a 1 hour incubation at room temperature with shaking at 50 rpm, 70 μl of bovine serum was added, and then the plates were incubated at 37° C. with shaking for 1 hour. Unbound phage were removed by washing 3 time with 300 μl of PBS-T. After the final wash, phage bound to stents were used to infect E. coli cells. The infected cells were incubated in 96 deep-well plates, containing 1 ml of growth medium (e.g., 2xYT+5 μg/ml tetracycline) per well, at 37° C. overnight with shaking. Amplified phage-containing supernatant from each well was harvested by centrifugation. Second, third, and fourth rounds of selection were performed in a similar manner to that of the first round, using 150 µl of amplified phage supernatant from the previous round as input, and diluted with 150 µl of PBS-T+1% BSA. From the fourth round of selection, 340 individual clonal phage were then isolated and tested by plating out dilutions of phage pools to obtain single plaques. To detect phage that specifically bound to a metal such as stainless steel, conventional ELISAs were performed using an anti-M13 phage antibody conjugated to horseradish-peroxidase, followed by the addition of chromogenic agent ABTS (2,2'-azinobis(3-ethylbenzthiazoline-6-sulfonic acid). Relative binding strengths of the phage were determined by testing serial dilutions of the phage for binding to stainless steel in an ELISA, using an anti-M13 phage antibody conjugated to horseradish-peroxidase, followed by the addition of chromogenic agent ABTS, and measuring the absorbance at 405 nm. In the ELISA for determining relative binding strengths, the phage titrations were done in either buffer alone, or buffer containing 20% whole blood. The DNA sequence encoding peptides that specifically bound a metallic surface was determined. The sequence encoding the peptide insert was located in the phage genome and translated to yield the corresponding amino acid sequence displayed on the phage surface.

From the phage titration experiments, three individual phage showed a desired relative binding specificity. Amino acid determination of the nucleic acid inserts in these 3 individual phage revealed that the phage represented 2 different peptide sequences (i.e., 2 of the 3 shared the same amino acid sequence), as shown in Table 1. Thus, Table 1 illustrates such surface-binding domains, having binding specificity for a metals, such as stainless steel of stents, and comprising peptides consisting essentially of amino acid sequences consisting of SEQ ID NO:1 and SEQ ID NO:2.

TABLE 1

Binding specificity for a metal such as stainless steel

| SEQ ID NO: | Amino acid sequence (single letter code) |
|---|---|
| 1 | SGVVDAGVVAEDGVSGEASRSSHRTNHKKNNPKKKNKTR |
| 2 | SVEVACVSAGGGSSDVCASRNHTISKNHKKKNKNSNKTR |
| 3 | SSHRTNHKKNNPKKKNKTR |
| 4 | NHTISKNHKKKNKNSNKTR |

B. Surface Binding Domain Characterizations and Modifications

Examination of the amino acid sequences (SEQ ID NO:1 and SEQ ID NO:2) of the two surface-binding domains revealed that in each, the C-terminal half of the peptide is rich in basic amino acids such as lysine and histidine. Therefore, to determine if the binding specificity for stainless steel is primarily due to the amino acids in the C-terminal half of the amino acid sequence, or if the N-terminal region also impacts binding, peptides consisting essentially of amino acid sequences illustrated as SEQ ID NO:3 and SEQ ID NO:4 were synthesized. The peptides, as listed in Table 2 as SEQ ID NOs: 1, 3, and 4 were each synthesized with a biotin tag, and then assayed for relative binding strengths by ELISA using similar methods as that used for determining the relative binding strengths of phage displaying the peptides (as previously described herein). In this assay, serial dilutions (ranging from 0 µM to 10 µM) of each of the peptides were incubated with the stainless steel stents, washed with PBS-T, and relative binding specificity was quantitated by detecting the colorometric signal resulting from the reaction of streptavidin-alkaline phosphatase (the streptavidin portion binding to the biotin-labeled peptides) with chromogenic substrate. The EC50 was determined from the titration curve. As illustrated in Table 2, a peptide consisting essentially of an amino acid sequence of SEQ ID NO:3 has the strongest binding specificity (or alternatively, binding affinity), as compared to a peptide consisting essentially of an amino acid sequence of either SEQ ID NO:1 or SEQ ID NO:4. Additionally, these results support that the amino acids in the C-terminal half rich in lysine and histidine (e.g., amino acids 21-39 of SEQ ID NO:1 which is illustrated by SEQ ID NO:3; and amino acids 21-39 of SEQ ID NO:2 (illustrated as SEQ ID NO:4)) are primarily responsible for the binding specificity of these peptides for a metal (e.g. titanium, and other metals having an oxide layer), and more preferentially for stainless steel.

TABLE 2

| SEQ ID NO: | EC50 expressed in nanomoles (nM) |
|---|---|
| 1 | <250 nM |
| 4 | <250 nM |
| 3 | <50 nM |

From these experiments and considering amino acids in key positions and their contributions for mediating binding specificity to a metal such as stainless steel, a preferred surface-binding domain comprising a peptide variant or derivative of a peptide having the amino acid sequence of any one of SEQ ID NOs: 1, 2, 3, or 4 comprises at least one peptide having a motif of SEQ ID NO:5, as follows.
SEQ ID NO:5: $X_1$—H—X—X—$X_2$—$X_2$—$X_2$—K—$X_1$—$X_1$—X—K—$X_1$—$X_1$—N—K; where
X is any amino acid;
$X_1$ is K, N, or S, but preferably either K or N; and
$X_2$ is K, N, or H.

Thus, a preferred surface-binding domain according to the present invention having binding specificity for metal such as stainless steel of a medical device comprises a peptide consisting essentially of an amino acid sequence illustrated by SEQ ID NO: 5.

Additional titration curves were generated from experiments in which a peptide consisting essentially of the amino acid sequence illustrated as SEQ ID NO:3 was subjected to ethylene oxide sterilization (642 mg/L for 2 hours). The results show that sterilization with ethylene oxide had minimal to no effect on the relative binding specificity for the peptide to stainless steel (approximately the same EC50, <50 nm, as from titration curves of the same peptide without being subjected to ethylene oxide sterilization).

A surface-binding domain comprising a peptide consisting essentially of the amino acid sequence illustrated as SEQ ID NO:3 was further modified to evaluate such parameters as the effect of pH on binding specificity, and the stability in plasma (e.g., in presence of proteases present in the plasma). In one example, a peptide consisting essentially of the amino acid sequence illustrated as SEQ ID NO:3 was synthesized with D-amino acids rather than L-amino acids (SEQ ID NO:6). In another example, synthesized were surface-binding domains comprising a multimer (a divalent version (SEQ ID NO:7), and a tetravalent version (SEQ ID NO:8)) of a peptide consisting essentially of the amino acid sequence illustrated as SEQ ID NO:3. These multimers of SEQ ID NO:3 are illustrated as follows.

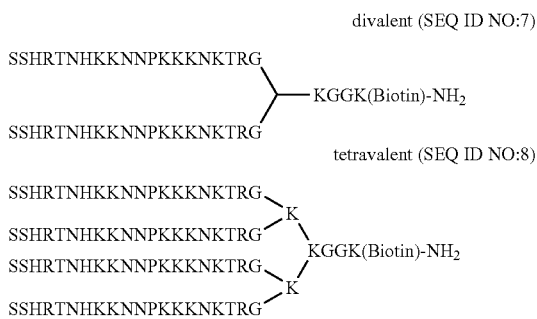

These multimers, SEQ ID NOs: 7 and 8, were synthesized as follows. Briefly, the multimers were built on a lysine MAP core and comprised of two and four peptide modules, respectively, of SEQ ID NO:3. This core matrix was used to generate dual and tetrameric branches of SEQ ID NO:3. The multimers were synthesized sequentially using solid phase chemistry on a peptide synthesizer. The synthesis was carried out at a 0.05 mmol scale which ensures maximum coupling yields during synthesis. The biotin reporter moiety was placed at the C-terminus of the molecule, and was appended by a short Gly-Gly-linker to the lysine core. Standard Fmoc/t-Bu chemistry was employed using AA/HBTU/HOBt/NMM (1:1:1:2) as the coupling reagents (AA is amino acid; HOBt is O-Pfp ester/1-hydroxybenzotriazole; HBTU is N-[1H-benzotriazol-1-yl] (dimethylamino) methylene]-N-methylmethanaminium hexafluorophosphate N-oxide; NMM is N-methylmorpholine). Amino acids were used in 5-10 fold excess in the synthesis cycles, and all residues were doubly, triply or even quadruply coupled depending upon the complexity of residues coupled. The coupling reactions were monitored by Kaiser ninhydrin test. The Fmoc deprotection reactions was carried out using 20% piperidine in dimethylformamide. Peptide cleavage from the resin was accomplished using trifluoracetic acid (TFA: $H_2O$:Triisopropylsilane=95:2.5:2.5) at room temperature for 4 hours. The crude product was precipitated in cold ether. The pellet obtained after centrifugation was washed thrice with cold ether and lyophilized to give a white solid as crude desired product. The crude products were analyzed by analytical high performance liquid chromatography (HPLC) on a C-18 column using mobile eluants (A=$H_2O$/TFA (0.1% TFA) and B=Acetonitrile/TFA (0.1% TFA). The multimers were also further analyzed by mass spectrometry for before subjecting each to final purification by HPLC. The fractions containing the desired product were pooled and lyophilized to obtain a fluffy white powder (>98% purity).

For determining the effect of pH on binding specificity, the assay for determining relative binding strengths (by ELISA) was performed in the presence of different buffers, varying in pH in a range of from pH 2 to pH 12. For example, a buffer containing glycine and water was adjusted to pH2 using HCl; an acetate buffer was adjusted to pH 4.0 (ionic strength of about 0.001 M); a phosphate buffer ($NaH_2PO_4$) was adjusted to pH 6.0 (ionic strength of about 0.012M); a phosphate buffer ($NaH_2PO_4$) was adjusted to pH 7.0 (ionic strength of about 0.019M); a tris buffer was adjusted to pH 8.0 (ionic strength of about 0.006M); an ethanolamine buffer was adjusted to pH 10.0 (ionic strength of about 0.003M); and a phosphate buffer ($NaH_2PO_4$) was adjusted to pH 12.0 (ionic strength of about 0.044M). The final concentration of each peptide in this assay was 1 µM. Tested in this assay were surface-binding domains comprising a peptide consisting essentially of the amino acid sequence illustrated as SEQ ID NO:3, and the multimers thereof (divalent version (SEQ ID NO:7) and tetravalent version (SEQ ID NO:8)). The binding curves showed that all three peptides (monvalent, divalent and tetravalent of the amino acid sequence of SEQ ID NO:3) bind well over the range of pH values from pH 6.0 to pH 8.0, with the optimum pH for binding being pH 7.0; and no more than a 20% decrease in binding at pH 6.0 or pH 8.0.

Peptides consisting essentially of a monvalent or tetravalent version (SEQ ID NO:8) of the amino acid sequence of SEQ ID NO:3, and a peptide comprising the D-amino acid version thereof (SEQ ID NO:6) were all tested in an ELISA binding assay essentially as described herein, but performed with stainless steel beads in the presence of plasma, to assess stability (one or more of susceptibility to proteases present in plasma, or ability to compete with plasma components in binding to stainless steel). Both the tetravalent version (SEQ ID NO:8) of the amino acid sequence of SEQ ID NO:3, and a peptide consisting essentially of the amino acid sequence illustrated in SEQ ID NO:6 showed significantly more stability (e.g., retaining from about 1.5 to about 4 times more peptide bound) in the presence of plasma, including less susceptibility to degradation by proteolytic enzymes, than a peptide consisting essentially of the amino acid sequence illustrated as SEQ ID NO:3.

EXAMPLE 3

This example illustrates the discovery and characterization of endothelial-binding domains comprising peptides having binding specificity for cells of endothelial cell lineage.

A. Phage Screening and Selections.

Phage libraries were pooled into four groups and screened for peptides that bind to human umbilical vein endothelial cells (HUVECs). The four pools were first pre-cleared on non-target cells (e.g., cells other than cells of endothelial cell lineage). For each pool, 10 µL of phage ($10^{10}$ of phage) was added to $1\times10^6$ cells of each of the following cell types: HEK-293 cells, aortic vascular smooth muscle cells (AoSMC), and platelets. The phage and cells were incubated for 1 hour at room temperature. Cells and attached phage were pelleted by centrifugation. The phage remaining in the supernatant were used for subsequent selections on HUVECs. Selections on HUVECS were performed using methods known in the art, including by one or more of biopanning with the cells including differential centrifugation, by fluorescence-activated cell sorting (FACS), and over cell monolayers.

Following selection on HUVECs, cells were rinsed in buffer and centrifuged. HUVECs with adherent phage were resuspended in 2 ml 2xYT bacterial culture medium and cultured with DH5αF' cells. Phage were separated from the bacterial culture medium and then tested on non-target and target cells using fluorescence-activated cell sorting (FACS) to confirm specificity. Cells and attached phage were resuspended in medium containing anti-M13 phage antibody conjugated to phycoerythrin. After washing, cells were resuspended in buffer+1% BSA, and analyzed by FACS for relative positivity. Using this process, identified are phage displaying peptides that have specificity for binding endothelial cells relative to smooth muscle cells and platelets (e.g., showing less than 10% positivity by FACS for smooth muscle cells and platelets). The phage DNA sequence insert encoding peptides that specifically bound the endothelial cells was determined, and then translated to yield the corresponding amino acid sequence displayed on the phage surface (without adjoining phage sequence; e.g., SS or SR). Table 3 illustrates such endothelial-binding domains comprising peptides consisting essentially of amino acid sequences consisting of SEQ ID NO:9-46. Amino acid sequences illustrated in Table 3 as SEQ ID NOs:39-46 were from a particular phage library favoring presence of the amino acid cysteine. However, from the amino acid sequences discovered from the other phage libraries (i.e., SEQ ID NOs: 9-38), most display relatedness in sequence through a rich concentration of amino acids glycine (G), valine (V), and alanine (A) (e.g., comprising no less than 10% and no more than about 75% of the amino acid residues in the sequence), which may be an indication of structure-function relationship. In that regard, it has been reported that peptides formed of glycine, alanine, valine, and aspartic acid have tertiary structures with potential catalytic functions.

TABLE 3

| SEQ ID NO: | Amino acid sequence Single letter code |
| --- | --- |
| 9 | GVDEWVGSSCAGVEECY |
| 10 | LFSSAFVFGALAGSGAG |
| 11 | FFGADSYLGGSFASAFD |
| 12 | GDVAASFFASAASAFSV |
| 13 | LAGAGWDAVVGGEGAVG |
| 14 | AGSSSSVSFVAAAGSAV |
| 15 | AVFVADVLGEEFVGAVA |
| 16 | GVGYGWYSVAASSVVSA |
| 17 | PFHTGAFLWPESHSHSH |
| 18 | SEYWSVGSVFAGSS |
| 19 | FYGEVGYVGASLYAGGAS |
| 20 | VVESSAAYASASSFAVV |
| 21 | FEGASVASLAFAGSVAG |
| 22 | VGAVSSSSLSEEFLGSL |
| 23 | YVGSAFSAAVASSVSEG |
| 24 | WAGAGSGGVAWSADFGV |
| 25 | SADVSAALLVLGASEVL |
| 26 | FAVYCASLSGVCSASFE |
| 27 | AGSSAFSVVASSVSVGG |
| 28 | YFRDATPAVFGYW |
| 29 | AYEDGFYSSGVVSSDWV |
| 30 | VSGFGFSDSGAGEGVF |
| 31 | GAWLVSALIERGVGAQW |
| 32 | VVFAASGVAADAGWSVS |
| 33 | QMRECDDCCCMVLPFTS |
| 34 | HNSPFFLDCNFDAPCL |
| 35 | GDLVTSTCLLGLCAERG |
| 36 | LSAGPLDWWSSLRSSAS |

TABLE 3-continued

| SEQ ID NO: | Amino acid sequence Single letter code |
| --- | --- |
| 37 | LFSLLPALAFLGEEQGP |
| 38 | ADSFVLASAGSVQVVVA |
| 39 | EGLVASVSCYAGGSCAVSR |
| 40 | SCNLPACFDILFRSLDKWS |
| 41 | SCNRDYNWLDSVGHCVN |
| 42 | SCLQWSFIGAYSSLSGQPS |
| 43 | SCSLCVLPSVTFDLKLECC |
| 44 | SSRISDYVGLSACPGGCAS |
| 45 | SCFCAILIKIIVFLSLVFS |
| 46 | CSTALKWTC |

B. Binding Domain Characterizations

Several of the endothelial-binding domains listed in Table 3 with desirable binding specificities (e.g., SEQ ID NOs: 9-18, 23-28, 30-32, and 35) were further characterized for binding to various cell types in whole blood by FACS, by synthesizing the peptides with a C-terminal biotin tag. Cells were harvested from cell culture flasks using trypsin/EDTA. The cells were neutralized with complete (serum-containing) media and allowed to recover at 37° C. for at least 20 minutes. Each cell type was labeled with its corresponding antibody, as set forth in Table 4, below, and incubated for 20 minutes at room temperature.

TABLE 4

Antibodies to Various Cell Types

| Cell Type | Antibody | Amount |
| --- | --- | --- |
| Endothelial cell (human or Porcine) | Anti-CD31-APC (APC is allophycocyanin) | 100 μL/10$^6$ cells |
| Endothelial progenitor cell | Rabbit anti-CD133, followed by anti-rabbit-APC | |
| Smooth muscle cell | Anti-alpha actin-APC | 100 μL/10$^6$ cells |
| Platelet | Anti-CD42b-APC | 100 μL/1 mL blood |

The antibody-labeled cells were rinsed twice by centrifugation using washing buffer (HBSS+1% BSA+0.1% sodium azide, sterile-filtered). One hundred (100) μL of whole blood was aliquotted into each well of a deep-well polypropylene plate. Peptides were added to each well to achieve the desired peptide concentration. Minimal volumes of cells (typically 10 μL of cells or approximately 50,000 cells) were added to each well. In experiments comparing relative binding of peptides to endothelial cells and platelets, two sets of samples were prepared: The first set of samples consisted of antibody-labeled endothelial cells in whole blood; the second set consisted of unlabeled endothelial cells and antibody-labeled platelets in whole blood. The plate was covered and incubated for 20 minutes at room temperature, with shaking. Red blood cells were lysed by adding 1 mL of FACS lysing solution, and the plate was covered and shaken for 15 minutes at room temperature. One (1) mL of room temperature washing buffer was added to each well, then centrifuged at less than 1500 rpm in a room temperature centrifuge. The wells were aspirated and filled with 1.5 mL of washing buffer, then centrifuged and aspirated again. Cells were re-suspended by adding 500 µL of streptavidin-AlexaFluor 532 at 1:500 dilution in media at room temperature. The plate was covered and incubated for 20 minutes at room temperature, then rinsed twice by centrifugation at less than 1500 rpm with room temperature washing buffer. Final suspensions of cells were prepared in 250 µL of washing buffer+50 µL of 4% paraformaldehyde. The samples were transferred to an analysis plate and analyzed for cell binding using FACS. In the analysis, controls for each cell type (with relevant antibody as per Table 4, but containing no peptide) were used to assess background fluorescence. Any signal above the "no peptide" control was considered the percent positive population.

The results of the binding characterization show that particularly preferred endothelial-binding domains comprise peptides consisting essentially of amino acid sequences of SEQ ID NOs: 10, 14-18, 23, 25-28, and 30-32. These endothelial-binding domains showed binding to one or more of human coronary endothelial cells, porcine coronary endothelial cells, and endothelial progenitor cells with binding specificity and selectivity approaching or exceeding 40% positivity by FACs, and less than 10% positivity (and often less than 5% positivity) with platelets and smooth muscle cells. Some of these endothelial-binding domains had binding specificity that appeared to prefer binding to endothelial progenitor cells as compared to endothelial cells (e.g., amino acid sequence SEQ ID NO:14), whereas others showed a preference for binding endothelial cells (e.g., amino acid sequence SEQ ID NO:32). Additional assays characterizing binding specificity show one or more of these preferred endothelial-binding domains (e.g., SEQ ID NO:19) has an EC50 of less than 10 µM.

EXAMPLE 4

As already described herein, in some instances, the binding domains comprising peptides according to the present invention also comprised modifications; i.e., were blocked at the N-terminus and/or at the C-terminus, and/or were linked to another peptide. Using these methods, for example, a surface-binding domain having binding specificity for a metallic surface of a medical device may be linked to an endothelial-binding domain, in forming a biofunctional coating composition according to the present invention. As apparent to one skilled in the art, a method of preference for linking a linker molecule to a binding domain will vary according to the reactive groups present on each molecule. Protocols for covalently linking two molecules using reactive groups are well known to one of skill in the art. As previously described herein, using methods well known to those skilled in the art, two binding domains may be coupled by a linker to form a biofunctional coating composition according to the present invention by synthesizing a single contiguous peptide comprising a first binding domain (e.g., a surface-binding domain), a linker comprising 3 or more amino acids (e.g., GSS), and a second binding domain (e.g., an endothelial-binding domain). The terms "first" and "second" are only used for purposes of ease of description, and is not intended to be construed as to limiting the order of the synthesis. In other words, the first binding domain may comprise an endothelial-binding domain, and the second binding domain may comprise the surface-binding domain. In an alternate method, at least one first binding domain having been avidinated (using streptavidin, avidin, or a functional derivative thereof, and methods known in the art) may be coupled to at least one second binding domain having been biotinylated (using biotin, and methods known in the art), in forming a biofunctional coating composition according to the present invention. In this example, the avidin-biotin molecules serve as the linker for coupling at least one surface-binding domain to at least one endothelial-binding domain in forming an interfacial biomaterial according to the present invention.

As an illustrative example of making the biofunctional coating composition according to the present invention, at least one surface-binding domain comprising a peptide consisting essentially of the amino acid sequence of SEQ ID NO:3 was linked to at least one endothelial-binding domain comprising a peptide consisting essentially of the amino acid sequence of SEQ ID NO:19. In one example, the surface-binding domain was coupled to the endothelial-binding domain via a linker comprising a 10 unit polyethylene glycol linker ("PEG"), to form a biofunctional coating composition comprising an amino acid sequence illustrated as SEQ ID NO:47 (a biotin tag was included as part of the PEG linker solely to facilitate detection during characterization of the biofunctional coating composition, as will be described herein; and the free C-terminal amino acid was amidated).

SEQ ID NO:47
SSFYGEVGYVGASLYAGGASSRG-PEG-SSHRTNHKKNNPKKKNKTRG

Briefly, the biofunctional coating composition was synthesized on a peptide synthesizer in linear fashion, and in the following order as one contiguous chain: an amino acid sequence of SEQ ID NO:3, the PEG linker, and an amino acid sequence of SEQ ID NO:19. Standard Fmoc/t-Bu chemistry was employed using AA/HBTU/HOBt/ NMM (1:1:1:2) as the coupling reagents. Amino acids were used in 5 fold excess in the synthesis cycles, and all residues were double coupled. The coupling reactions were monitored by Kaiser ninhydrin test. In order to inhibit peptide aggregation, pseudoproline Fmoc-Ala-Ser(Psi Me,Me pro)-OH was employed, and was also double coupled in 5 fold excess. Fmoc-Lys(Biotin)-OH and Fmoc-NH-(Peg)10-COOH were double coupled manually using the above coupling conditions in order to produce a PEG linker with the biotin tag. The Fmoc deprotection reactions were carried out using 20% piperidine in DMF. The biofunctional coating was cleaved from the resin by using Reagent K (TFA:EDT:$H_2$O:phenol: thioanisole =82.5:2.5:5: 5:5) at room temperature for 4 hours to yield a crude product. The crude product was precipitated in cold ether. The pellet obtained after centrifugation was washed thrice with cold ether, and then lyophilized to give a white solid as crude product. The crude product was analyzed by analytical HPLC and by mass spectrometry, and then was purified by HPLC using a gradient of buffer B (Acetonitrile /TFA (0.1%TFA)). The desired product, the biofunctional coating composition, was pooled and lyophilized in obtaining a fluffy white powder (>95% purity).

Using methods similar to those described in Examples 2 and 3 herein, the biofunctional coating composition comprising the amino acid sequences of SEQ ID NO:47 was tested in a binding specificity assay by titrating the concentrations of the biofunctional coating composition and measuring the relative binding to a metal comprising stainless steel. Briefly, stainless steel beads were blocked with buffer (PBS-T with 1% BSA), washed, and then incubated with the biofunctional coating composition at concentrations from 0 to 10 µM for 1 hour at room temperature. After washing, the amount of biofunctional coating composition was detected with streptavidin-alkaline phosphatase (the streptavidin portion binding to the biotin-labeled biofunctional coating composition) with chromogenic substrate. The EC50 was determined from the titration curve. The biofunctional coating composition comprising an amino acid sequence illustrated as SEQ ID NO:47 bound to stainless steel with similar binding activity (e.g., EC50) as the surface-binding domain from which it was made (a surface-binding domain comprising a peptide consisting essentially of the amino acid sequence of SEQ ID NO:3).

The biofunctional coating composition comprising an amino acid sequence illustrated as SEQ ID NO:47 was then tested for its ability to selectively adhere cells of endothelial cell lineage to a metallic surface of a medical device. In this example, stainless steel disks were used to represent a metallic surface of a medical device. The disks were contacted with a buffered solution containing the biofunctional coating composition at a concentration of 10 µM for 1 hour at room temperature. As controls for non-specific binding, disks were either uncoated, or coated with the surface-binding domain comprising a peptide consisting essentially of an amino acid sequence of SEQ ID NO:3, or an irrelevant peptide (having no known binding specificity for metal or stainless steel or endothelial cells). The disks were washed with PBS, and then 25,000 endothelial cells were added in cell media containing 10% bovine serum, and incubated at room temperature for 15 minutes. The disks were washed in PBS, and the cells were then quantitated using a commercial luminescent cell viability assay system that measures intracellular ATP using a luminescent read-out. The luminescence was detected using a plate reader. The biofunctional coating composition comprising an amino acid sequence illustrated as SEQ ID NO:47 showed the ability to bind endothelial cells to the metallic surface by demonstrating a several fold increase in the number of endothelial cells bound to disks, as compared to any of the controls.

EXAMPLE 5

In this example, illustrated are methods according to the present invention: (a) a method for manufacturing a medical device; (b) a method of coating a metallic surface of a medical device so as to render the coated surface capable of adhering to cells of endothelial cell lineage; (c) a method for promoting endothelialization of at least one metallic surface of a medical device; and (d) a method for promoting the adherence of cells of endothelial cell lineage to a medical device. The methods comprise contacting at least one metallic (and more preferably stainless steel) surface of a medical device with an effective amount of a biofunctional coating composition under conditions suitable to produce a coating on the metallic surface, wherein the biofunctional coating composition comprises at least one surface-binding domain and at least one endothelial-binding domain; wherein the at least one surface-binding domain comprises a peptide consisting essentially of an amino acid sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, and a combination thereof; wherein the at least one endothelial-binding domain comprises a peptide consisting essentially of an amino acid sequence selected from the group consisting of SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, and a combination thereof; and wherein the at least one surface-binding domain is coupled to the at least one endothelial-binding domain. Preferably, the at least one surface-binding domain is covalently coupled to the at least one endothelial-binding domain via a linker. The at least one surface-binding domain is the component of the biofunctional coating composition which is primarily responsible for binding the biofunctional coating composition to the one or more surfaces of the medical device to be coated.

With respect to these methods according to the present invention, and with respect to a biofunctional coating composition according to the present invention, and wherein at least one surface of the medical device to be coated comprises more than one metallic material (e.g., two different metals; a metal and a metal oxide; a metal and metal alloy; and the like), the at least one surface-binding domain in the biofunctional coating may comprise a plurality (two or more) of types of surface-binding domains, wherein each type of surface-binding domain has binding specificity for a different surface material to be coated, as compared to the other surface-binding domains of which the biofunctional coating composition is comprised. Also with respect to this method according to the present invention, and with respect to a biofunctional coating composition according to the present invention, the at least one endothelial-binding domain may comprise more than one type (e.g., as determined by binding specificity of each type of endothelial-binding domain; for example, two or more different peptides, one peptide with binding specificity for endothelial cells, the other peptide with binding specificity for endothelial progenitor cells).

In these methods according to the present invention, when the biofunctional coating composition is contacted with the at least one metallic surface of the medical device to be coated, either (a) the at least one endothelial-binding domain is bound to cells of endothelial cell lineage; or (b) the at least one endothelial-binding domain is not yet bound to cells of endothelial cell lineage. With respect to the latter, in a further step of coating, the coated surface of the medical device is then contacted with a sufficient amount of cells of endothelial cell lineage (in vitro or in vivo), for which the at least one endothelial-binding domain has binding specificity, under conditions suitable so that cells of endothelial cell lineage bind to the at least one endothelial-binding domain. In one example, the medical device may be contacted with cells of endothelial cell lineage (autologous or from a donor (e.g., allogeneic or xenogeneic) in vitro for the cells to bind and adhere to the coated surface of the device, and subsequently the device is implanted.

In another example, in a method according to the present invention for promoting endothelialization of a vascular device, generally one or more metallic surfaces of the device to be exposed to vasculature once the device is implanted in an individual, is the one or mores surfaces of device desired and selected to be coated by a biofunctional coating composition according to the present invention. The method comprises the steps of: (a) contacting a biofunctional coating composition according to the present invention to at least one surface of a vascular device desired to be endothelialized, so that the biofunctional coating composition becomes bound to the at least one metallic surface, in forming a coated surface on the device; wherein the biofunctional coating composition comprises at least one surface-binding domain coupled to at least one endothelial-cell binding domain; and (b) implanting the device into an individual in need of the device; wherein cells of endothelial cell lineage (produced by the individual, and circulating in the individual's vasculature) contact and attach to the coated surface of the device (via the biofunctional coating composition), wherein such contact and attachment promotes spread of cells of endothelial cell lineage over the coated surface of the device, in promoting endothelialization of the vascular device. Promoting endothelialization on the implanted device may further promote one or more of healing of tissue or vasculature adjacent to the implanted device, promote incorporation (integration) of the implanted device into the adjacent tissue, and reduce occurrence of thrombosis as related to the implanted device.

Conventional processes known in the art may be used to apply the biofunctional coating composition according to the present invention to the one or more metallic surfaces of the medical device to be coated (in contacting the biofunctional coating composition with the one or more surfaces). Such processes are known to include, but are not limited to, dipping, brushing, spraying, vapor deposition, and electro-deposition. Formulations of the biofunctional coating composition according to the present invention may depend on the process used for coating the medical device. For example, a solution or suspension comprising the biofunctional coating composition may be applied through the spray nozzle of a spraying device, creating droplets that coat the metallic surface of the medical device to be coated. The medical device is allowed to dry, and may then be further processed prior to use (e.g., washed in a solution (e.g., water or isotonic buffer) to remove excess biofunctional coating composition; by sterilization using any one or methods known in the art for sterilizing medical devices; etc.). Alternatively, the biofunctional coating composition and the medical device may all be sterilized prior to the process, and the process performed under sterile conditions.

In another process for applying the biofunctional coating to one or more metallic surfaces of a medical device to be coated, the surface of the medical device to be coated is dipped into a liquid (e.g., solution or suspension, aqueous or solvent) containing the biofunctional coating composition in an amount effective to coat the surface. For example, the surface is dipped or immersed into a bath containing the biofunctional coating composition. Suitable conditions for applying the biofunctional coating composition include allowing the surface to be coated to remain in contact with the liquid containing the biofunctional coating composition for a suitable period of time (e.g., ranging from about 5 minutes to about 12 hours; more preferably, ranging from 15 minutes to 60 minutes), at a suitable temperature (e.g., ranging from 10° C. to about 50° C.; more preferably, ranging from room temperature to 37° C.). The coated medical device may then be further processed, as necessary for use (washing, sterilization, and the like).

In another process for applying the biofunctional coating to one or more metallic surfaces of a medical device to be coated, the biofunctional coating composition according to the present invention is formulated in a dry powder (e.g., via air drying or lyophilizing the biofunctional coating composition). The powder comprising the biofunctional coating composition is then applied using methods known in the art for powder-coating the surface of the medical device to be coated. Typically, once applied, such powder coatings are then heat-treated (e.g., using infrared heating means) to complete the application process.

However, these illustrative processes for applying a biofunctional coating composition to a surface of a medical device are not exclusive, as other coating and stabilization methods may be employed (as one of skill in the art will be able to select the compositions and methods used to fit the needs of the particular device and purpose). For example, where the surface of the medical device to be coated is metallic in nature, a hydrophilic polymer (as previously described herein in more detail) may be used in conjunction (either applied simultaneously, or subsequently, to application of the biofunctional coating composition according to the present invention) so long as the biofunctional coating composition on the metallic surface of the medical device substantially retains its function to bind to cells of endothelial cell origin in promoting one or more of adherence and endothelialization on the coated surface. In continuing this illustration, because of the elastomeric nature of the hydrophilic polymer, it may add to the stability of the biofunctional coating composition bound to the surface of the medical device should the device be subjected to mechanical forces or stress. Thus, the methods and compositions according to the present invention may also be used in conjunction with drug-eluting medical devices, or other coating technologies which provide one or more functional benefits to medical devices not provided by the biofunctional coating compositions according to the present invention.

Additionally, in a method according to the present invention, a coat comprising the biofunctional coating composition may be stabilized, for example, by air drying or by lyophilization. However, these treatments are not exclusive, and other coating and stabilization methods may be employed. Suitable coating and stabilization methods are known in the art. For example, the at least one metallic surface of the vascular device to be coated with the biofunctional coating composition of the present invention may be pre-treated prior to the coating step so as to enhance one or more of the binding of the surface-binding domain to the material comprising the surface to be coated, and the consistency and uniformity of the coating. For example, such pretreatment may comprise etching or plasma treating the surface material of the device to be coated so as to make the surface more hydrophilic, in enhancing the binding of a surface binding domain comprising some hydrophobic amino acids in its amino acid sequence which interact with the hydrophilic moieties on the surface as part of binding specificity interactions.

In addition, or alternatively, in a further step, the at least one metallic surface of the vascular device coated with the biofunctional coating composition of the present invention may be treated, subsequent to coating but prior to implantation into an individual, so as to enhance endothelialization of the coated surface. For example, a matrix or layer of a biological substrate which supports endothelialization, and particularly growth (including proliferation) of endothelial cells adhering to the coated surface, may be added to (e.g., overlayed and/or adsorbed onto) the coated surface (for example, prior to or subsequent to binding and attachment to the coated surface by cells of endothelial cell lineage). Components of such layer or matrix can include a vascular biologic comprising one or more of collagen (e.g., type IV and/or type V), vitrogen, laminin, entactin, fibronectin, glycans (e.g., proteoglycans, glycosaminoglycans), and growth factors supporting endothelial cell growth (e.g., VEGF, EGF, FGF, heparin-binding epidermal-like growth factor, and the like).

Thus, in accordance with these methods of the present invention, a medical device may first be treated by a process which enhances binding (e.g., by increasing the hydrophilicity of, or the molecular adhesiveness of, the at least one metallic surface of the device) of the biofunctional coating composition to the at least one treated surface of the device; contacting the biofunctional coating with the at least one treated surface in binding the biofunctional coating composition to the at least one treated surface in forming a coated surface. The method may further comprise contacting a vascular biologic with the coated surface in an amount effective to promote endothelialization on the coated surface. The methods may further comprise, prior to the implantation of the device, a step of contacting the coated device with cells of endothelial cell lineage in promoting one or more of attachment or adherence of the cells of the endothelial cell lineage, support for endothelial cell growth, and support for endothelial cell differentiation. For example, cells of the endothelial cell lineage may be purified and isolated using methods known in the art. For example, progenitor endothelial cells may be isolated from human peripheral blood using magnetic separation comprising magnetic beads coated with antibody to CD34. In another example, human umbilical vein endothelial cells may be isolated from umbilical cords by collagenase treatment of the blood vessel walls to release the endothelial cells, which may then be cultured in suitable supporting culture medium known in the art.

EXAMPLE 6

It is apparent to one skilled in the art, that based on the amino acid sequence of the peptide comprising a preferred endothelial-binding domain and/or surface binding domain used in accordance with the present invention, that polynucleotides (nucleic acid molecules) encoding such a peptide (or variants thereof as described herein) may be synthesized or constructed, and that such a peptide may be produced by recombinant DNA technology as a means of manufacture (e.g., in culture) and/or in vivo production by introducing such polynucleotides in vivo. For example, it is apparent to one skilled in the art that more than one polynucleotide sequence can encode a peptide consisting essentially of an amino acid sequence of SEQ ID NO:3 according to the present invention, and that such polynucleotides may be synthesized on the bases of triplet codons known to encode the amino acids of a peptide consisting essentially of the amino acid sequence of SEQ ID NO:3, third base degeneracy, and selection of triplet codon usage preferred by the host cell, typically a prokaryotic cell or eukaryotic cell (e.g., bacterial cells such as E. coli; yeast cells; mammalian cells; avian cells; amphibian cells; plant cells; fish cells; and insect cells; whether located in vitro or in vivo.) in which expression is desired. It would be routine for one skilled in the art to generate the degenerate variants described above, for instance, to optimize codon expression for a particular host (e.g., change codons in the bacteria mRNA to those preferred by a mammalian, plant or other bacterial host such as E. coli).

For purposes of illustration only, and not limitation, provided as SEQ ID NO:48 is a polynucleotide encoding an amino acid sequence of SEQ ID NO:3, from which, as apparent to one skilled in the art, codon usage will generally apply to polynucleotides encoding a preferred surface-binding domain comprising a peptide consisting essentially of the amino acid sequence illustrated in SEQ ID NO:3. Also provided as SEQ ID NO:49 is a polynucleotide encoding an amino acid sequence of SEQ ID NO:19, from which, as apparent to one skilled in the art, codon usage will generally apply to polynucleotides encoding a preferred endothelial-binding domain comprising a peptide consisting essentially of the amino acid sequence illustrated in SEQ ID NO:19. Thus, for example, using SEQ ID NO:48 in relation to SEQ ID NO:3 and SEQ ID NO:49 in relation to SEQ ID NO:19, one skilled in the art could readily construct a polynucleotide encoding variants of the amino acid sequence illustrated in SEQ ID NO:3 or SEQ ID NO:19, or encoding any one or more of the other amino acid sequences provided by the present invention (e.g., SEQ ID NOs: 1-2, and 4-18, and 20-47).

In one illustrative embodiment, provided is a prokaryotic expression vector containing a polynucleotide encoding an endothelial cell binding domain for use in accordance with the present invention; and its use for the recombinant production of a peptide comprising the endothelial-binding domain. In one example, the polynucleotide may be positioned in a prokaryotic expression vector so that when the peptide is produced in bacterial host cells, it is produced as a fusion protein with other amino acid sequence (e.g., which assist in purification of the peptide; or as recombinantly coupled to a surface-binding domain). For example, there are sequences known to those skilled in the art which, as part of a fusion protein with a peptide desired to be expressed, facilitates production in inclusion bodies found in the cytoplasm of the prokaryotic cell used for expression and/or assists in purification of fusion proteins containing such sequence. Inclusion bodies may be separated from other prokaryotic cellular components by methods known in the art to include denaturing agents, and fractionation (e.g., centrifugation, column chromatography, and the like). In another example, there are commercially available vectors into which is inserted a desired nucleic acid sequence of interest to be expressed as a protein or peptide such that upon expression, the gene product also contains a plurality of terminal histidine residues ("His tags") that can be utilized in the purification of the gene product using methods standard in the art.

It is apparent to one skilled in the art that a nucleic acid sequence encoding a binding domain (endothelial-binding domain, or surface-binding domain, or a combination thereof) comprising a peptide for use according to the present invention can be inserted into, and become part of a, nucleic acid molecule comprising a plasmid, or vectors other than plasmids; and other expression systems can be used including, but not limited to, bacteria transformed with a bacteriophage vector, or cosmid DNA; yeast containing yeast vectors; fungi containing fungal vectors; insect cell lines infected with virus (e.g. baculovirus); and mammalian cell lines having introduced therein (e.g., transfected or electroporated with) plasmid or viral expression vectors, or infected with recombinant virus (e.g. vaccinia virus, adenovirus, adeno-associated virus, retrovirus, etc.). Successful expression of the peptide requires that either the recombinant nucleic acid molecule comprising the encoding sequence of the peptide, or the vector itself, contain the necessary control elements for transcription and translation which is compatible with, and recognized by the particular host system used for expression.

Using methods known in the art of molecular biology, including methods described above, various promoters and enhancers can be incorporated into the vector or the recombinant nucleic acid molecule comprising the encoding sequence to increase the expression of the peptide, provided that the increased expression of the peptide is compatible with (for example, non-toxic to) the particular host cell system used. As apparent to one skilled in the art, the selection of the promoter will depend on the expression system used. Promoters vary in strength, i.e., ability to facilitate transcription. Generally, for the purpose of expressing a cloned gene, it is desirable to use a strong promoter in order to obtain a high level of transcription of the gene and expression into gene product. For example, bacterial, phage, or plasmid promoters known in the art from which a high level of transcription has been observed in a host cell system comprising E. coli include the lac promoter, trp promoter, T7 promoter, recA promoter, ribosomal RNA promoter, the P.sub.R and P.sub.L promoters, lacUV5, ompF, bla, lpp, and the like, may be used to provide transcription of the inserted nucleotide sequence encoding the synthetic peptide. Commonly used mammalian promoters in expression vectors for mammalian expression systems are the promoters from mammalian viral genes. Examples include the SV40 early promoter, mouse mammary tumor virus LTR promoter, adenovirus major late promoter, herpes simplex virus promoter, and the CMV promoter.

In the case where expression of the peptide may be lethal or detrimental to the host cells, the host cell strain/line and expression vectors may be chosen such that the action of the promoter is inhibited until specifically induced. For example, in certain operons the addition of specific inducers is necessary for efficient transcription of the inserted DNA (e.g., the lac operon is induced by the addition of lactose or isopropylthio-beta-D-galactoside ("IPTG"); trp operon is induced when tryptophan is absent in the growth media; and tetracycline can be use in mammalian expression vectors having a tet sensitive promoter). Thus, expression of the peptide may be controlled by culturing transformed or transfected cells under conditions such that the promoter controlling the expression from the encoding sequence is not induced, and when the cells reach a suitable density in the growth medium, the promoter can be induced for expression from the encoding sequence. Other control elements for efficient gene transcription or message translation are well known in the art to include enhancers, transcription or translation initiation signals, transcription termination and polyadenylation sequences, and the like.

The foregoing description of the specific embodiments of the present invention have been described in detail for purposes of illustration. In view of the descriptions and illustrations, others skilled in the art can, by applying, current knowledge, readily modify and/or adapt the present invention for various applications without departing from the basic concept of the present invention; and thus, such modifications and/or adaptations are intended to be within the meaning and scope of the appended claims.

What is claimed is:

1. A biofunctional coating composition comprising at least one binding domain that specifically binds to a metallic surface material of a medical device ("surface-binding domain"), and at least one binding domain that specifically binds to cells of endothelial cell lineage ("endothelial-binding domain"); wherein the surface-binding domain comprises a peptide having a length of 16 to 60 amino acids comprising SEQ ID NO:5, and wherein the peptide can be modified to comprise one or more terminal modifications, and a modification to facilitate linking; wherein the endothelial-binding domain comprises a peptide having a length of 18 to 60 amino acids comprising SEQ ID NO:19; and wherein the peptide can be modified to comprise one or more terminal modifications, and a modification to facilitate linking, or one or more conservative substitutions in SEQ ID NO:19, and wherein the surface-binding domain is coupled to the endothelial-binding domain.

2. The biofunctional coating composition according to claim 1, wherein the endothelial-binding domain is bound to cells of endothelial cell lineage.

3. The biofunctional coating composition according to claim 1, wherein the biofunctional coating composition comprises more than one endothelial-binding domain.

4. The biofunctional coating composition according to claim 1, wherein the cells of endothelial cell lineage, for which the endothelial-binding domain has binding specificity, comprise cells selected from the group consisting of endothelial cells, endothelial progenitor cells, and a combination thereof.

5. The biofunctional coating composition according to claim 1, wherein the biofunctional coating composition comprises more than one surface-binding domain.

6. The biofunctional coating composition according to claim 1, wherein the metallic surface material, for which the surface-binding domain has binding specificity, comprises a material selected from the group consisting of a metal, a metal oxide, a metal alloy, and a combination thereof.

7. The biofunctional coating composition according to claim 1, wherein the metallic surface material, for which the surface-binding domain has binding specificity, comprises stainless steel.

8. The biofunctional coating composition according to claim 1, wherein the surface binding domain comprises a multimer of the peptide.

9. The biofunctional coating composition according to claim 1, wherein the surface-binding domain and the endothelial-binding domain are coupled together via a linker.

10. An endothelial-binding domain comprising a peptide having a length of 18 to 60 amino acids comprising SEQ ID NO:19 and wherein the peptide can be modified to comprise one or more terminal modifications, and a modification to facilitate linking, or one or more conservative substitutions in SEQ ID NO:19.

11. A surface-binding domain comprising a peptide having a length of 16 to 60 amino acids comprising SEQ ID NO:5, and wherein the peptide can be modified to comprise one or more terminal modifications, and a modification to facilitate linking.

12. The surface-binding domain according to claim 11, wherein the surface-binding domain comprises a multimer of the peptide.

13. The biofunctional coating composition according to claim 1, wherein the surface-binding domain comprises SEQ ID NO:1, SEQ ID NO:2, SEQ ID NO:3, SEQ ID NO:4, SEQ ID NO:6, SEQ ID NO:7, or SEQ ID NO:8.

14. A method for coating at least one metallic surface of a medical device, the method comprising contacting the at least one metallic surface of the medical device with a biofunctional coating composition according to claim 1 to form a coating on the at least one surface; and wherein the endothelial-binding domain is in an amount effective for adhering cells of endothelial cell lineage to the coating on the at least one metallic surface.

15. The method according to claim 14, wherein the medical device comprises a vascular device.

16. The method according to claim 15, wherein the vascular device comprises a stent.

17. The method according to claim 14, wherein the surface-binding domain and the endothelial-binding domain are coupled via a linker.

18. The method according to claim 14, wherein the surface-binding domain comprises a multimer of the peptide.

19. The method according to claim 14, wherein endothelial-binding domain is bound to cells of endothelial cell lineage.

20. The method according to claim 14, wherein the biofunctional coating composition comprises more than one endothelial-binding domain.

21. The method according to claim 14, wherein the biofunctional coating composition comprises more than one surface-binding domain.

22. The method according to claim 14, wherein the surface-binding domain has an amino acid sequence of SEQ ID NO:1, SEQ ID NO:2, SEQ ID NO:3, SEQ ID NO:4, SEQ ID NO:6, SEQ ID NO:7, or SEQ ID NO:8.

* * * * *